United States Patent [19]

Otaka et al.

[11] Patent Number: 5,134,368
[45] Date of Patent: Jul. 28, 1992

[54] APPARATUS FOR MAGNETICALLY DETECTING DEGRADATION OF METAL MATERIAL USING SUPERCONDUCTOR SENSOR SYSTEM AND REFERENCE MATERIAL DATA COMPARISON

[75] Inventors: Masahiro Otaka, Hitachi; Kunio Enomoto, Ibaraki; Kunio Hasegawa, Katsuta; Makoto Hayashi, Hitachi; Tasuku Shimizu, Hitachi; Kazuo Takaku, Hitachi, all of Japan

[73] Assignee: Hitachi, Ltd., Tokyo, Japan

[21] Appl. No.: 611,426

[22] Filed: Nov. 8, 1990

Related U.S. Application Data

[62] Division of Ser. No. 247,414, Sep. 21, 1988, Pat. No. 5,059,903.

[30] Foreign Application Priority Data

| Sep. 21, 1987 | [JP] | Japan | 62-234828 |
| Nov. 4, 1987 | [JP] | Japan | 62-277445 |
| Dec. 4, 1987 | [JP] | Japan | 62-305656 |

[51] Int. Cl.⁵ .................. G01R 33/12; G01R 33/035; G01N 27/72; G21C 17/003
[52] U.S. Cl. .................. 324/224; 324/219; 324/226; 324/227; 324/240; 324/241; 324/248; 324/262
[58] Field of Search ............... 324/202, 209, 219–228, 324/232–243, 248, 262; 376/245, 249; 505/843, 846; 364/481, 506–508, 550, 550.01, 556, 571.04

[56] References Cited

U.S. PATENT DOCUMENTS

| 3,528,001 | 9/1970 | Yntema | 324/248 X |
| 3,646,813 | 3/1972 | Kuznietz et al. | 324/248 X |
| 4,324,255 | 4/1982 | Barach et al. | 324/248 X |
| 4,692,701 | 9/1987 | Dundas et al. | 324/209 X |
| 4,746,858 | 5/1988 | Metala et al. | 324/228 X |

FOREIGN PATENT DOCUMENTS

| 0141653 | 11/1980 | Japan | 324/227 |
| 0028859 | 2/1986 | Japan | 324/227 |
| 0119756 | 5/1989 | Japan | 324/248 |
| 0078983 | 3/1990 | Japan | 324/248 |

OTHER PUBLICATIONS

Nave et al.; Micromagnetic susceptometer, *Rev. Sci. Instrum.*, vol. 51, No. 5, May 1980, pp. 591–596.
Ishizuka et al.; A Squid Magnetometer . . . around the Magnetic Phase Transition Point, *Japanese Jour. of Appl. Physics*, vol. 19, No. 4 Apr. 1980 pp. 639–646.

*Primary Examiner*—Gerard R. Strecker
*Attorney, Agent, or Firm*—Antonelli, Terry, Stout & Kraus

[57] ABSTRACT

On the basis of a finding that a magnetic hysteresis of a metal material, among magnetization characteristics changing with secular degradation of the metal material, shows a clear correspondence with the degree of degradation of the metal material, a change in such a magnetization characteristic is measured to estimate the degree of secular degradation of the metal material. In a typical embodiment, a superconducting quantum interference device is used to detect the magnetization characteristic of a measuring object. According to the present invention, the degree of embrittlement of a metal material used in an environment of high temperatures can be quickly detected in a non-destructive fashion so that the danger of brittle fracture of the metal material can be reliably prevented.

1 Claim, 27 Drawing Sheets

FIG. 33
(a)
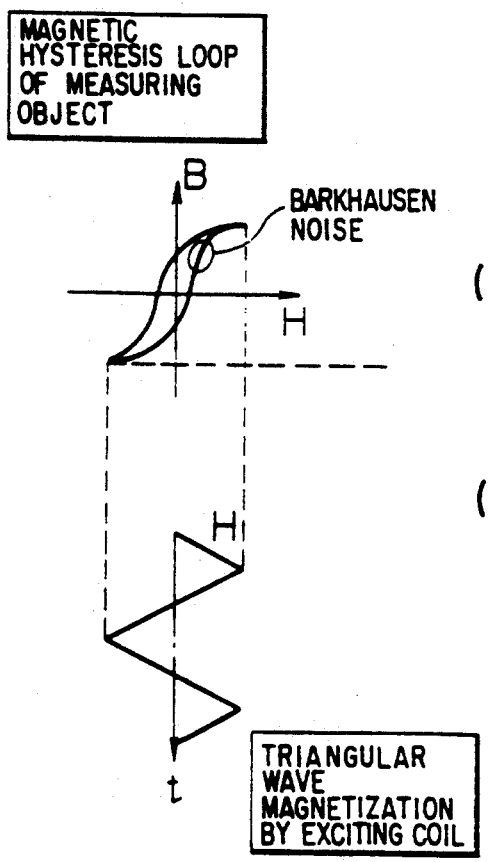
(b)
(c)
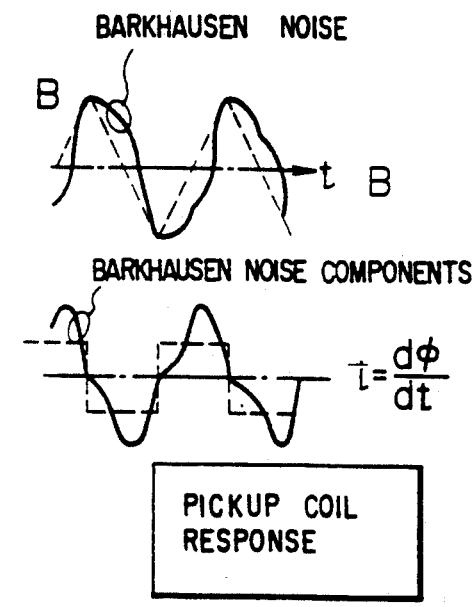
FIG. 34
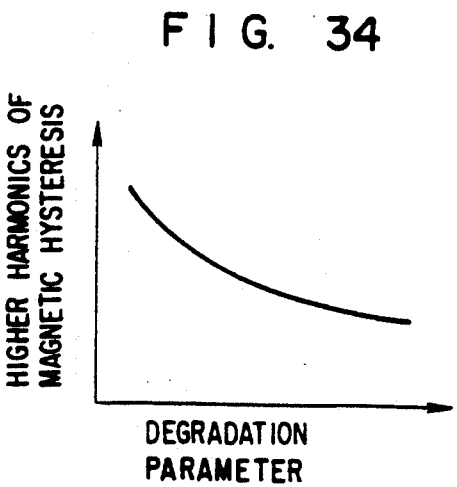
FIG. 35
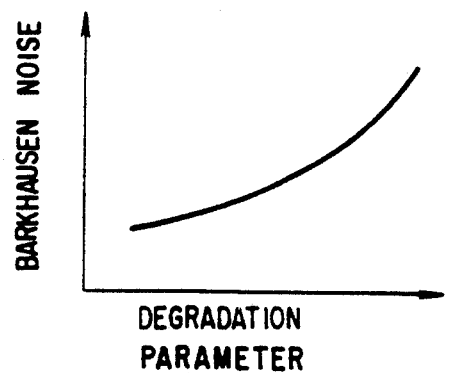

APPARATUS FOR MAGNETICALLY DETECTING DEGRADATION OF METAL MATERIAL USING SUPERCONDUCTOR SENSOR SYSTEM AND REFERENCE MATERIAL DATA COMPARISON

This is a divisional of application Ser. No. 247,414, filed Sep. 21, 1988, now U.S. Pat. No. 5,059,903.

BACKGROUND OF THE INVENTION

1. Field of the Invention

This invention relates to a method and apparatus for detecting degradation of a metal material. More particularly, this invention relates to a degradation measuring method and apparatus suitable for detecting embrittlement due to high-temperature aging, of practical plant components of a metal material such as a ferritic stainless steel used in an environment of high temperatures such as that encountered in a chemical plant and a nuclear power plant.

2. Description of the Prior Art

Methods of measuring embrittlement of a metal material are disclosed in, for example, JP-A-54-61981 and JP-A-61-28859. According to one of the prior art methods disclosed in JP-A-54-61981, a weld metal such as an austenitic stainless steel is decided to become brittle when the amount of δ-ferrite has decreased by more than 5% of its initial value. Also, according to the prior art method disclosed in JP-A-61-28859, a change in a magnetic characteristic of a measuring object is measured to detect degradation of the measuring object.

Further, JP-A-56-168545 discloses a method in which a magnetic characteristic of a measuring object is utilized to monitor the metallographic structure of the measuring object, and JP-A-59-108970 discloses a method of detecting a magnetic characteristic itself of a measuring object.

As disclosed in JP-A-54-61981 cited above, it is already known that aging degradation occurs on a metal material, especially, a ferritic stainless steel, when the stainless steel is used for a long period of time at high temperatures. That is, at a relatively high temperature higher than about 600° C., σ-embrittlement attributable to precipitation of a σ-phase occurs, while in a temperature range of from 400° C. to 500° C., so called 475° C.-embrittlement occurs. However, this 475° C.-embrittlement may occur even when the ferritic stainless steel is used for a long period of time in a temperature range lower than 400° C. Therefore, it is necessary to give sufficient consideration to the use of practical plant components of the ferritic stainless steel at high temperatures. However, the tendency to become brittle at temperatures lower than 500° C. was not taken into consideration in the prior art disclosure cited above, and the 475° C.-embrittlement could not be detected.

Further, the initial amount of ferrite in practical welded parts differs depending on the position of the welds and tends to greatly fluctuate. Furthermore, because the number of welds in a practical plant is very large, it is difficult to monitor the initial amount of ferrite for each of all of the welds and all of equipments. Thus, the prior art method disclosed in JP-A-54-61981 could not be put into practical use in a practical plant because it was not applicable to parts where the initial amount of ferrite was unknown.

On the other hand, an eddy current test method (referred to hereinafter as an ECT) is disclosed in, for example, JP-A-55-141653. According to this prior art method, an ECT value of a measuring object, which is, for example, an iron alloy, is compared with an ECT value of the measuring object measured before practical use or an ECT value of the same material as the material of the measuring object and subjected to heat treatment similar to initial heat treatment applied to the measuring object, and the degree of degradation of the iron alloy is decided depending on whether the result of comparison is positive or negative. However, a quantitative measurement or analysis could not be made because the decision is merely based on whether the result of comparison is positive or negative.

In the prior art method disclosed in JP-A-61-28859, it is necessary to measure the initial value of a magnetic characteristic of a measuring object. Also, the prior art methods disclosed in JP-A-59-108970 and JP-A-56-168545 are merely directed to measurement of magnetic characteristics of metal materials and cannot be utilized for detection of the degree of degradation of the metal materials.

SUMMARY OF THE INVENTION

It is an object of the present invention to provide a method and apparatus which can detect, with high accuracy and in a non-destructive method, the degree of embrittlement of a practical plant member of a metal material such as a ferritic stainless steel used in an environment of high temperatures.

According to the present invention which attains the above object, magnetization characteristics of a metal material changing as a result of deterioration due to aging of the metal material are measured to decide the degree of degradation of the metal material. The configuration of a magnetic hysteresis, which is representative of magnetization characteristics of a measuring object of a metal material, shows a clear correspondence with the degree of degradation of the metal material. Thus, by detecting a change in this magnetic characteristic, the degree of degradation of the measuring object of the metal material can be estimated. Further, by means of statistical data processing such as a regression analysis, the degree of degradation of the metal material can be estimated with a high rate of correlation.

An exciting coil in the form of a coil of a superconducting material can be used for efficiently magnetizing the measuring object.

Further, although the combination of a detecting coil and an integrator is commonly employed for detecting a magnetic field, a magnetic sensor device including a superconducting quantum interference device (SQUID) or a semiconductor Hall element capable of magnetic measurement with high accuracy can be used in lieu of the combination described above.

In accordance with a first aspect of the present invention, there is provided a method of detecting degradation of a measuring object by applying a magnetic field to the measuring object, measuring a change in a peculiar magnetic characteristic of the measuring object, and detecting the degree of degradation of the measuring object on the basis of the result of measurement of the change in the magnetic characteristic of the measuring object, the method comprising the steps of previously computing the relation between changes in the magnetic characteristic and degradation of the measuring object, estimating the magnetic characteristic of the measuring object in an as-received material on the basis of the above relation, measuring the magnetic characteristic of the measuring object during use, computing the change from the estimated magnetic characteristic to the measured magnetic characteristic, and comparing the computed change in the magnetic characteristic with the above relation between the magnetic characteristic and the degradation to decide the degree of deterioration of the measuring object at the time of measurement.

In accordance with a second aspect of the present invention, there is provided a method of detecting degradation of a measuring object by applying a magnetic field to the measuring object, measuring a change in a peculiar magnetic characteristic of the measuring object and detecting the degree of degradation of the measuring object on the basis of the result of measurement of the change in the magnetic characteristic of the measuring object, the method comprising the steps of previously measuring magnetic hysteresis loops of the measuring object while changing the magnetizing force, normalizing the data of the magnetic hysteresis loops, measuring a magnetic characteristic of the measuring object during use, and comparing the data of the measured magnetic characteristic with the data of the normalized magnetic characteristic to estimate the degree of degradation of the measuring object at the time of measurement. Thus, the degree of degradation of the measuring object can be estimated without requiring initial data of the measuring object in its unused virgin state.

In accordance with a third aspect of the present invention, there is provided a degradation detecting apparatus comprising means for applying a magnetic field to a measuring object, means for detecting a magnetic characteristic of the measuring object, and an arithmetic processing device deciding the degree of degradation of the measuring object on the basis of a change in the magnetic characteristic of the measuring object due to application of the magnetic field, the arithmetic processing device including a data base storing previously acquired data of the relation between changes in the magnetic characteristic and degradation of the measuring object, a first arithmetic processing part estimating the magnetic characteristic of the measuring object in an unused virgin state on the basis of the data stored in the data base, and a second arithmetic processing part computing the change from the estimated magnetic characteristic to the detected magnetic characteristic on the basis of the data stored in the data base to generate the degree of degradation of the measuring object as an output. It is apparent that an apparatus for estimating the degree of degradation of a measuring object on the basis of normalized data as disclosed in the second method described above belongs also to the scope of the present invention.

In accordance with a fourth aspect of the present invention, there is provided a degradation detecting apparatus comprising means for applying a magnetic field to a measuring object, and a magnetic characteristic measuring device measuring a magnetic characteristic of the measuring object so as to detect the degree of degradation of the measuring object on the basis of a change in the magnetic characteristic of the measuring object due to application of the magnetic field, the magnetic characteristic measuring device including an exciting coil in the form of a superconducting coil, a magnetization sensor disposed at the center of the exciting coil, the sensor being operable at low temperatures, a fluidtight container of a heat insulating material containing the entirety of at least the exciting coil and the magnetization sensor, and a cooling system for cooling the superconducting system, the apparatus further comprising means for previously computing the relation between the magnetic characteristic and degradation of the measuring object and comparing the detected magnetic characteristic of the measuring object with the above relation to decide the degree of degradation of the measuring object at the time of detection. It is apparent that an apparatus for estimating the degree of degradation of a measuring object on the basis of normalized data as disclosed in the second method described above belongs also to the scope of the present invention.

In accordance with a fifth aspect of the present invention, there is provided a degradation evaluating apparatus comprising means for applying a magnetic field to a sample taken from a part of a measuring object, means for detecting a magnetic characteristic of the sample, and an arithmetic processing device deciding the degree of degradation of the sample on the basis of a change in the magnetic characteristic of the sample due to application of the magnetic field, the arithmetic processing device including a data base storing previously acquired data of the relation between changes in the magnetic characteristic and degradation of the sample, a first arithmetic processing part estimating the magnetic characteristic of the sample on the basis of the data stored in the data base by assuming that the sample is a part of an unused virgin measuring object, and a second arithmetic processing part computing the change from the estimated magnetic characteristic to the detected magnetic characteristic on the basis of the data stored in the data base to generate the degree of degradation of the measuring object as an output. It is apparent that an apparatus for estimating the degree of degradation of a measuring object on the basis of normalized data as disclosed in the second method described above belongs also to the scope of the present invention.

In accordance with a sixth aspect of the present invention, there is provided a degradation evaluating apparatus comprising means for applying a magnetic field to a sample, and a magnetic characteristic measuring device measuring a magnetic characteristic of the sample so as to detect the degree of degradation of the sample on the basis of a change in the magnetic characteristic of the sample due to application of the magnetic field, the magnetic characteristic measuring device including an exciting coil in the form of a superconducting coil, a magnetization sensor in the form of a superconducting quantum interference device having a superconducting pickup coil of differential type disposed at the center of the exciting coil, the superconducting pickup coil of differential type defining thereinside a space into which the sample can be inserted from the outside, a fluidtight container of a heat insulating material containing the entirety of at least the exciting coil and the magnetization sensor, and a cooling system of coolant recirculating type for cooling the superconducting system, the apparatus further comprising means for previously computing the relation between the magnetic characteristic and degradation of the sample and comparing the detected magnetic characteristic of the sample with the above relation to decide the degree of degradation of the sample at the time of detection. It is apparent that an apparatus for evaluating the degree of degradation of a measuring object on the basis of normalized data as disclosed in the second method described above belongs also to the scope of the present invention.

In accordance with a seventh aspect of the present invention, there is provided an apparatus for inspecting degradation of a metal material comprising an exciting system and a sensor system including means for applying a magnetic field to a measuring object, and a magnetic characteristic measuring device measuring a magnetic characteristic of the measuring object to detect the degree of degradation of the measuring object on the basis of a change in the magnetic characteristic of the measuring object due to application of the magnetic field, the magnetic characteristic measuring device including an exciting coil in the form of a superconducting coil, a magnetization sensor disposed at the center of the exciting coil, the sensor being operable at low temperatures, a fluidtight container of a heat insulating material containing the entirety of at least the exciting coil and the magnetization sensor, and a cooling system of a type recirculating a coolant for cooling the superconducting system.

In accordance with an eighth aspect of the present invention, there is provided an apparatus for evaluating the degree of degradation of a very small sample taken from a part of a measuring object, comprising means for applying a magnetic field to the sample, and a magnetic characteristic measuring device measuring a magnetic characteristic of the sample, the magnetic characteristic measuring device including an exciting coil in the form of a superconducting coil, a magnetization sensor in the form of a superconducting quantum interference device having a superconducting pickup coil of differential type disposed at the center of the exciting coil, the superconducting pickup coil of differential type defining thereinside a space into which the sample can be inserted, a fluidtight container of a heat insulating material containing the entirety of at least the exciting coil and the magnetization sensor, and a cooling system of a type recirculating a coolant for cooling the superconducting system.

In accordance with a ninth aspect of the present invention, there is provided an apparatus for inspecting degradation of a metal material used in a nuclear reactor by means of magnetic diagnosis, comprising cable means for suspending the inspecting apparatus from a crane located above a reactor container so that internal equipments of the reactor container can be inspected, and a fluidtight inspection driver including vacuum-actuated attachments for fixing the inspecting apparatus to the inner wall of a pressure vessel of the reactor, and means for actuating three-dimensional scanning movements of the inspecting apparatus.

In accordance with a tenth aspect of the present invention, there is provided an apparatus for inspecting degradation of a metal material of pipes of a primary piping system of a nuclear reactor by means of magnetic diagnosis, comprising an inspection driver including means for moving the inspecting apparatus in the axial direction of a pipe, means for moving the inspecting apparatus in the circumferential direction of the pipe, and magnetic shielding means for minimizing magnetic noise.

In accordance with an eleventh aspect of the present invention, there is provided an apparatus for inspecting degradation of a metal material, comprising means for applying a magnetic field to a measuring object, and a magnetic characteristic measuring device measuring a magnetic characteristic of the measuring object with high accuracy so as to detect the degree of degradation of the measuring object on the basis of a change in the magnetic characteristic of the measuring object due to application of the magnetic field, the magnetic characteristic measuring device including a superconducting quantum interference device capable of detecting the magnetic characteristic of the measuring object, and a pickup coil of a normal conducting material associated with the superconducting quantum interference device.

In accordance with a twelfth aspect of the present invention, there is provided an apparatus for detecting degradation of a metal material, comprising means for applying a magnetic field to a measuring object and then demagnetizing to produce a residual magnetism in the measuring object, a high-sensitivity magnetization sensor sensing the residual magnetism, a data base storing previously acquired data of the relation between changes in the residual magnetism and degradation of the measuring object, and a computer deciding the degree of degradation of the measuring object on the basis of the data stored in the data base.

MEANS FOR APPLYING MAGNETIC FIELD

An exciting coil is a typical example of means for applying a magnetic field to a measuring object. This exciting coil is preferably in the form of a superconducting coil so that the measuring object can be efficiently magnetized to the level of magnetic saturation.

MAGNETIC CHARACTERISTICS

A magnetic hysteresis characteristic is a typical example of magnetic characteristics of a measuring object.

For example, a plurality of parameters of a magnetic hysteresis loop (such as, the area of the magnetic hysteresis loop, residual magnetic flux density and saturating magnetizing force) of a metal material are detected, and the relation between changes in the plural parameters of the magnetic hysteresis loop and degradation of the metal material is previously computed. An arithmetic data processing device is preferably used to carry out statistical data processing such as a regression analysis of those data so as to decide the degree of degradation of the measuring object.

As another example, a plurality of parameters of a magnetic hysteresis loop (such as, the area of the magnetic hysteresis loop, residual magnetic flux density and saturating magnetizing force) of a metal material are detected so as to normalize fluctuations of the parameters in an unused virgin state of the metal material, and the relation between changes in the plural normalized parameters and degradation of the metal material is previously computed. An arithmetic data processing device is preferably used to carry out processing of those data so as to decide the degree of degradation of the measuring object.

UNUSED MATERIAL

The term "unused material" is used in this specification to indicate that a specific metal material has not been used yet, that is, to indicate that the metal material is received in its as-received material. The initial amount of ferrite is, for example, the basis for identification that a metal material is received in an unused initial state.

AUXILIARY EQUIPMENTS

A demagnetizing device is an example of incidental equipments. Preferably, a measuring object is demagnetized, and, after the demagnetization, is magnetized while changing the magnetizing force to obtain a plurality of magnetic hysteresis loops for detecting changes in the plural parameters of each magnetic hysteresis loop such as the area of the magnetic hysteresis loop, residual magnetic flux density and saturating magnetizing force. An arithmetic data processing device is used to decide the degree of degradation of the metal material on the basis of the detected changes.

Another example of the auxiliary equipments is an exciting device of feedback controlled type. Preferably, the maximum magnetic flux density of a magnetic hysteresis loop to be measured is selected, and an exciting device of feedback controlled type is provided so as to detect the magnetic hysteresis loop of a metal material by means of feedback control of the magnetizing force with high accuracy. Further, when a superconducting quantum interference device is used, it is preferably shielded by both a magnetic shield and a radiation shield.

ARITHMETIC PROCESSING DEVICE

An arithmetic data processing device preferably used in the present invention includes a data base storing data showing an exact correspondence between various patterns of magnetic hysteresis loops and the degree of degradation of a metal material. After normalization of a measured magnetic hysteresis loop of a measuring object, the pattern of the magnetic hysteresis loop most analogous to the measured magnetic hysteresis loop is read out from the data base, and the arithmetic data processing device decides the degree of degradation of the measuring object. More concretely, the material of the measuring object is magnetized to the level of magnetic saturation to obtain a plurality of magnetic hysteresis loops of different patterns, and data showing an exact correspondence between the patterns of the magnetic hysteresis loops and the degree of degradation of the measuring object are stored in the data base. After normalization of a measured magnetic hysteresis loop of the measuring object, the pattern of the magnetic hysteresis loop most analogous to the measured magnetic hysteresis loop is read out from the data base, and the arithmetic data processing device decides the degree of degradation of the measuring object.

Another arithmetic data processing device preferably used in the present invention detects higher harmonic distortion components of a magnetic hysteresis loop of a metal material by the Fourier transformation and decides the degree of degradation of the metal material on the basis of a change in the values of the higher harmonic distortion components.

Another preferable arithmetic data processing device makes frequency analysis of data measured by a superconducting quantum interference device to decide the degree of degradation of a measuring object on the basis of a change in Barkhausen noise components.

CRITERION OF DEGRADATION

The criterion of degradation will be described in detail later in the specification. For example, a decrease in the value of fructure toughness of a metal material due to a change in its metallographic structure can be conveniently used as the criterion of degradation.

MAGNETIZATION SENSOR

A most preferable magnetization sensor is a superconducting quantum interference device. For example, it is preferable and convenient to employ an exciting system and a magnetization sensor system in which a superconducting quantum interference device is used to accurately detect a change in the magnetism.

Also, for the purpose of detection of a residual magnetism of a measuring object, a semiconductor Hall element can be used in lieu of the superconducting quantum interference device capable of magnetic detection with high accuracy.

When a metal material is used for a long period of time in an environment of a high temperature, a change generally occurs in its internal structure, resulting in a decreased mechanical strength. Especially, in the case of a ferritic stainless steel, its mechanical strength decreases markedly with the increase in the period of aging heat treatment at a high temperature.

The inventors made researches and studies on the tendency toward embrittlement of a metal material such as a ferritic stainless steel due to heating at high temperatures. As a result of the researches and studies, the inventors found that, with the progress of aging at high temperatures, the electromagnetic characteristics such as the electrical resistivity $\rho$ and permeability $\mu$ of the metal material were subjected to a change, and the mechanical properties such as the hardness and metallographic structure of the metal material were also subjected to a change. Especially, the inventors found that the tendency toward brittleness of the metal material shows a clear correspondence with a change in the magnetization characteristic of the metal material. The inventors measured a magnetic hysteresis of the metal material in an unused virgin state and that of the metal material in a state treated at a high temperature. As a result of the above measurements, the inventors found that the area of the magnetic hysteresis loop (the magnetic hysteresis loss) and the residual magnetic flux density were subjected to a change which was dependent on the degree of brittleness of the measuring object. Thus, when such a phenomenon is utilized, the progress of the tendency toward brittleness of a metal material, such as, a ferritic stainless steel, can be detected with high accuracy.

According to the present invention, the degree of brittleness of a metal material used at high temperatures can be detected quickly in a non-destructive way. Therefore, a rupture failure of such a metal material can be prevented before it occurs, and the safety of a practical plant member of such a metal material can be improved.

BRIEF DESCRIPTION OF THE DRAWINGS

FIG. 33 illustrates the basic principle of the operation of the rf SQUID shown in FIG. 32.

FIG. 34 is a graph showing the relation between higher harmonic components of a magnetic signal and a degradation parameter of a metal material.

FIG. 35 is a graph showing the relation between Barkhausen noise components of the magnetic signal and the degradation parameter of the metal material.

DESCRIPTION OF THE PREFERRED EMBODIMENTS

GENERAL SYSTEM ARRANGEMENT OF FIRST EMBODIMENT

Figure 1:
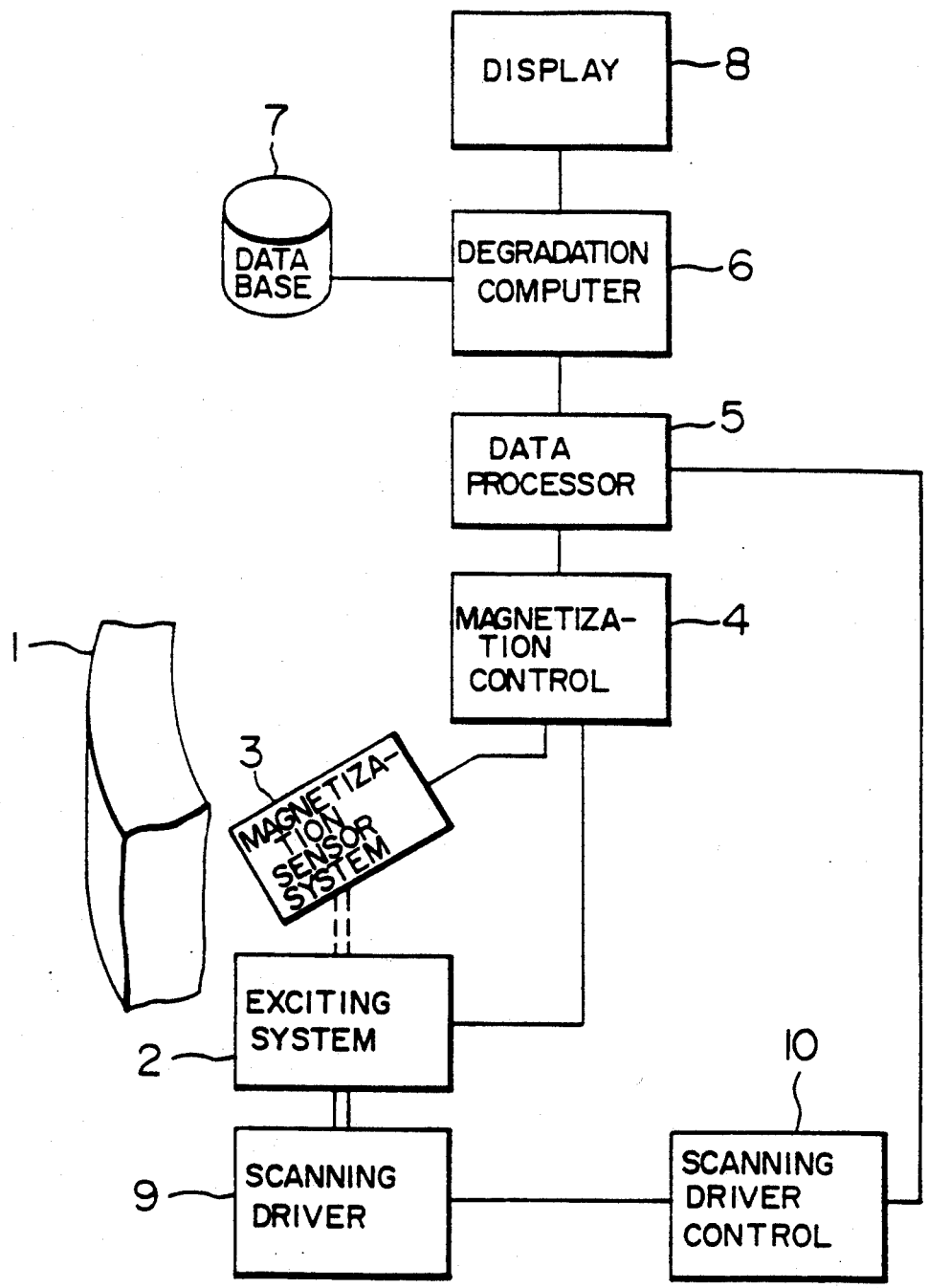
FIG. 1 is a general block system diagram showing an embodiment of the degradation detecting apparatus according to the present invention.

FIG. 1 shows one form of a general system arrangement employed for putting into practical use a first embodiment of the apparatus of the present invention for detecting degradation of a metal material.

Referring to FIG. 1, a measuring object 1 is a member such as a part of an equipment or a piping system of a plant such as a nuclear power plant. An exciting system 2 magnetizes the measuring object 1, and a magnetic sensor system 3 detects the magnetization. The apparatus further includes a magnetization control unit 4, a data processing unit 5, a degradation computing unit 6, a data base 7 and a display unit 8. A scanning driver 9 drives the exciting system 2 and magnetization sensor system 3 for scanning movement under control of a scanning driver controller 10.

The exciting system 2 and the magnetization sensor system 3 are disposed opposite to the surface of the measuring object 1. The scanning driver 9 for driving the scanning movement of the exciting system 2 and magnetization sensor system 3 is electrically connected to the scanning driver controller 10 to be controlled by the controller 10.

The exciting system 2 and the magnetization sensor system 3 are electrically connected to the magnetization control unit 4 to magnetize the measuring object 1 and detect the magnetization under control of the control unit 4. The data of magnetization and the data of the detected magnetization are supplied to the magnetization control unit 4 which sets the optimum conditions for the magnetization. The data processing unit 5 processes the acquired data for each of individual degradation parameters. The data processed in the data processing unit 5 for each of the individual degradation parameters are compared in the degradation computing unit 6 with corresponding data previously computed and stored as part of the data base 7, and, after necessary computation in the computing unit 6, the degree of degradation of the measuring object 1 is decided. The result of decision is displayed on the display unit 8.

EXCITING SYSTEM AND MAGNETIZATION SENSOR SYSTEM

Figure 2:
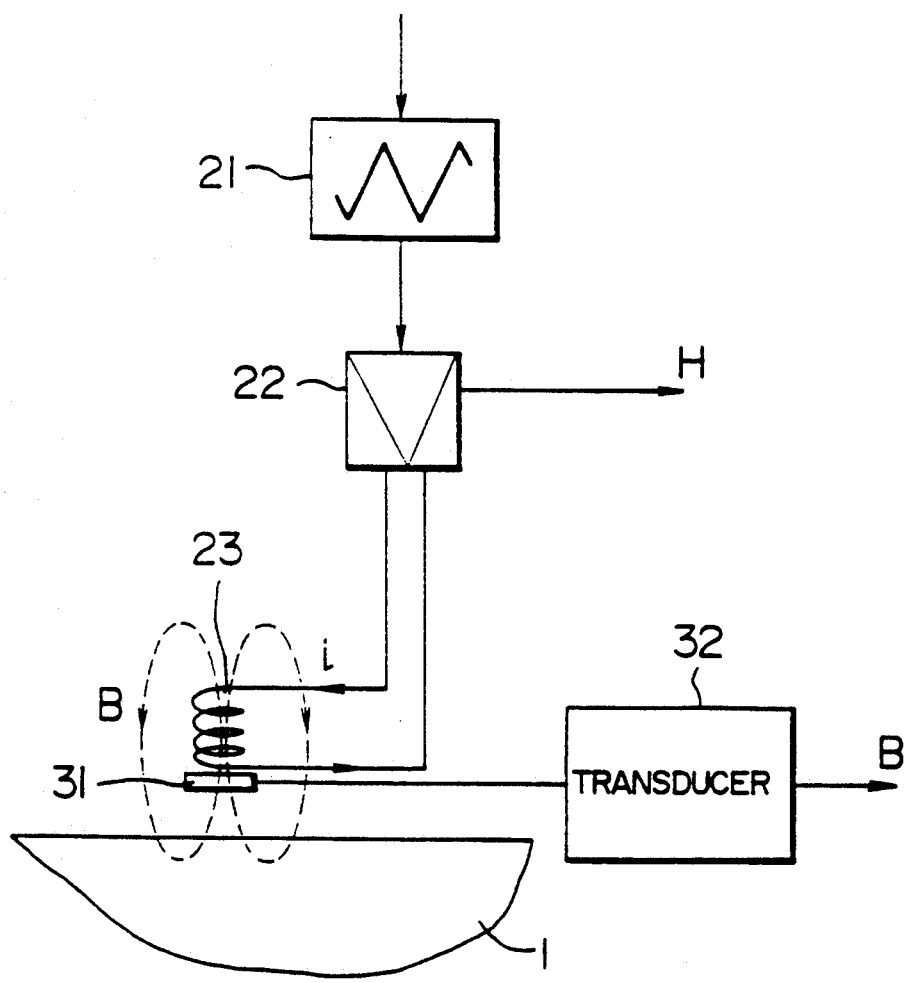
FIG. 2 shows the internal structure of the exciting system and magnetization sensor system used in the embodiment shown in FIG. 1.

FIG. 2 shows in detail the structure of the exciting system 2 and magnetization sensor system 3. Referring to FIG. 2, the exciting system 2 includes an oscillator 21 of waveform control type for controlling the waveform of a magnetizing current used for magnetization, an amplifier 22 for amplifying the oscillation output signal of the oscillator 21 and an exciting coil 23 for magnetizing the measuring object 1. From the amplifier 22, a signal indicative of the magnetizing force of the exciting coil 23 is generated. This signal is applied to the magnetization control unit 4. The symbol i designates the exciting current. A magnetic flux B flowing out from the exciting coil 23 to flow into the measuring object 1 is sensed by a magnetization sensor 31. The output of the magnetization sensor 31 is applied through a transducer 32 to the magnetization control unit 4.

MAGNETIZATION CONTROL UNIT

Figure 3:
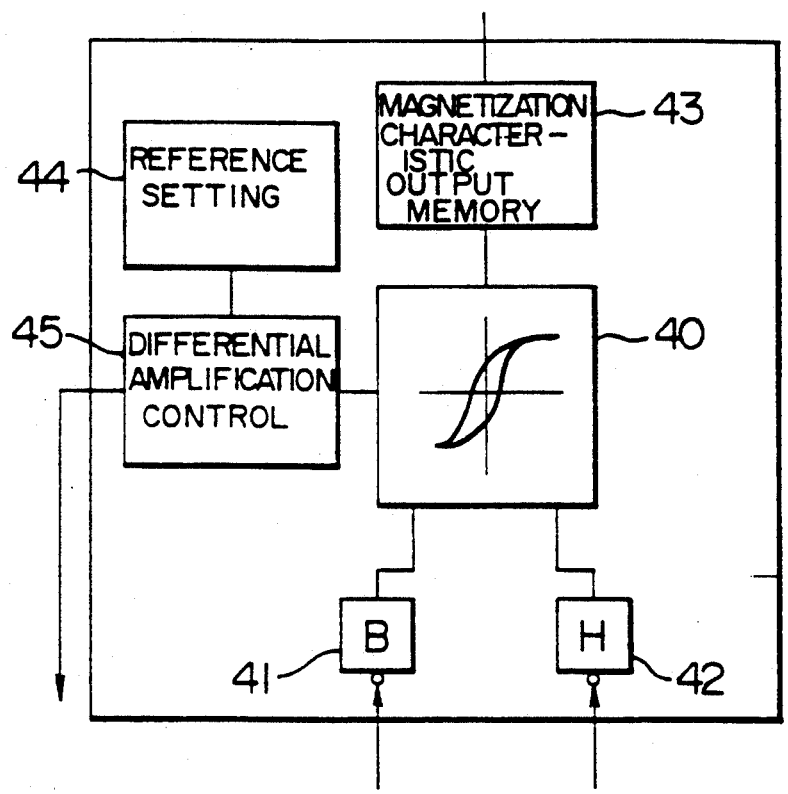
FIG. 3 shows the internal structure of the magnetization control unit used in the embodiment shown in FIG. 1.

FIG. 3 shows in detail the structure of the magnetization control unit 4. Referring to FIG. 3, the magnetization control unit 4 includes a magnetic hysteresis loop synthesizer 40, a flux density input interface 41, a magnetic field intensity input interface 42, a magnetization characteristic output memory 43, a reference setting device 44 and a differential amplification controller 45.

The data of the magnetic field intensity generated from the exciting system 2 for magnetizing the measuring object 1 is supplied through the magnetic field intensity input interface 42 to the magnetic hysteresis loop synthesizer 40. The data output of the magnetization sensor system 3, which may be composed of a Hall element or a detection coil and an integrator for sensing the magnetic flux induced by the magnetic field intensity, is supplied through the magnetic flux density input interface 41 to the magnetic hysteresis loop synthesizer 40. These data are synthesized into the corresponding magnetic hysteresis loop in the magnetic hysteresis loop synthesizer 40. This synthesized magnetic hysteresis loop is compared with a pre-set reference pattern stored in the reference setting device 44, and the difference or deviation is amplified by the differential amplification controller 45. The resultant output of the controller 45 is fed back to the exciting system 2 so as to establish the optimum exciting conditions. The data of the optimized magnetic hysteresis loop is supplied to the data processing unit 5 through the magnetization characteristic output memory 43.

SCANNING DRIVER

The detailed structure of the scanning driver 9 for driving the scanning movement of the exciting system 2 and magnetization sensor system 3 shown in FIG. 1 will be described with reference to FIGS. 4 and 6 when the present invention is applied to a boiling water type nuclear reactor.

Figure 4:
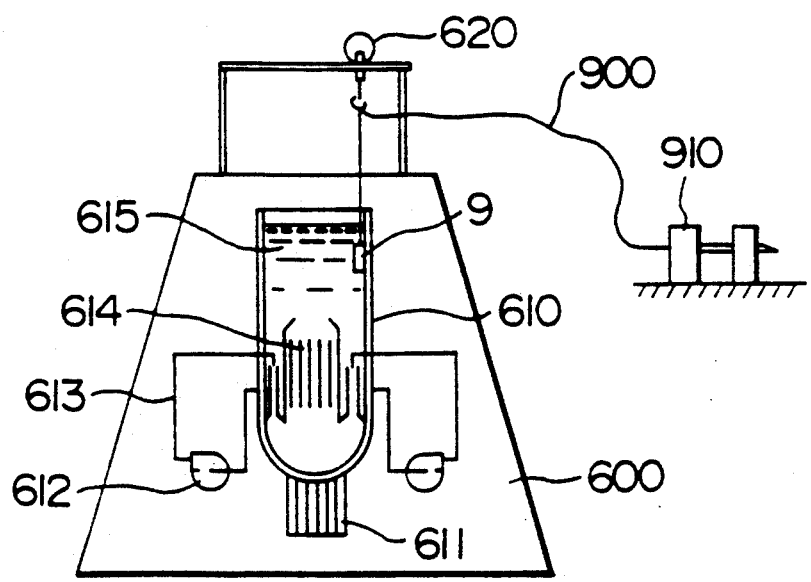
FIG. 4 is a schematic sectional view of a boiling water type nuclear reactor to which the embodiment shown in FIG. 1 is applied.

FIG. 4 is a schematic sectional view of a boiling water type nuclear reactor. Referring to FIG. 4, the boiling water type nuclear reactor includes a reactor container 600, a reactor pressure vessel 610, control rods 611, a recirculating feedwater pump 612, a primary piping system 613, a reactor core 614 and a reactor water pool 615. A crane 620 is located above the reactor container 600. The scanning driver 9 is suspended from the crane 620 in such a relation that the scanning driver 9 is disposed adjacent to the inner wall of the reactor pressure vessel 610 and immersed in the reactor water pool 615. The scanning driver 9 is electrically connected by cables 900 to, for example, a controller 910 disposed outside the reactor container 600 so that the scanning driver 9 can be remote-controlled.

Figure 6:
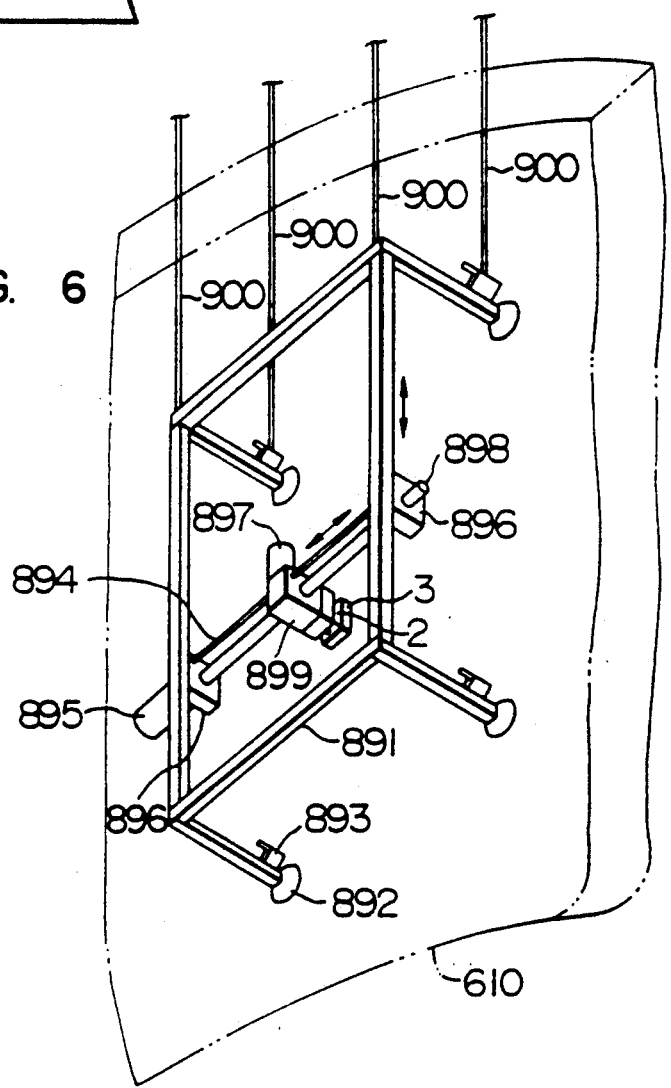
FIG. 6 is a perspective view of one form of the X-Y scanning driver used in the nuclear reactor shown in FIG. 4 for inspecting the inner wall of the pressure vessel of the nuclear reactor.

FIG. 6 shows one form of the scanning driver 9. More precisely, FIG. 6 shows the structure of an X-Y scanning type driver 9 for inspecting the inner wall of the reactor pressure vessel 610 of the boiling water type nuclear reactor shown in FIG. 4. The scanning driver 9 includes a frame 891 having four legs, vacuum-actuated attachments 892 and vacuum pumps 893 for fixing the frame 891 to the inner wall of the reactor pressure vessel 610, an X-axis motor 895, gear boxes 896 and a drive shaft 898 for moving the exciting system 2 and the magnetization sensor system 3 with respect to the frame 891 along the X-axis, and a Y-axis motor 897, an air cylinder 899 equipped with a gear box and a drive shaft 894 for moving the the exciting system 2 and the magnetization sensor system 3 with respect to the frame 891 along the Y-axis. The exciting system 2 and the magnetization sensor system 3 are mounted on one end of the air cylinder 899.

Another form of the scanning driver 9 when applied to a primary piping system of a boiling water type nuclear reactor will be described with reference to FIGS. 5, 7 and 8.

Figure 5:
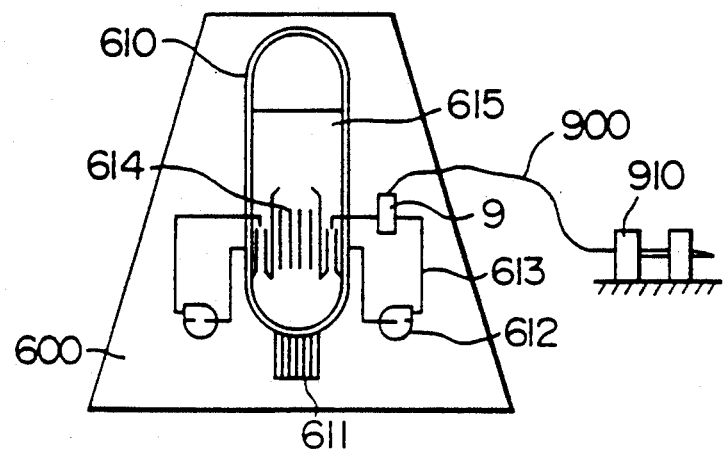
FIG. 5 is a schematic sectional view of another boiling water type nuclear reactor to which the embodiment shown in FIG. 1 is applied.

FIG. 5 is a schematic sectional view of a boiling water type nuclear reactor similar to that shown in FIG. 4. In FIG. 5, like reference numerals are used to designate like parts appearing in FIG. 4.

Referring to FIG. 5, the scanning driver 9 is disposed on a primary piping system 613. The scanning driver 9 is electrically connected by cables 900 to, for example, a controller 910 disposed outside a reactor container 600 to be remote-controlled by the controller 910.

Figure 7:
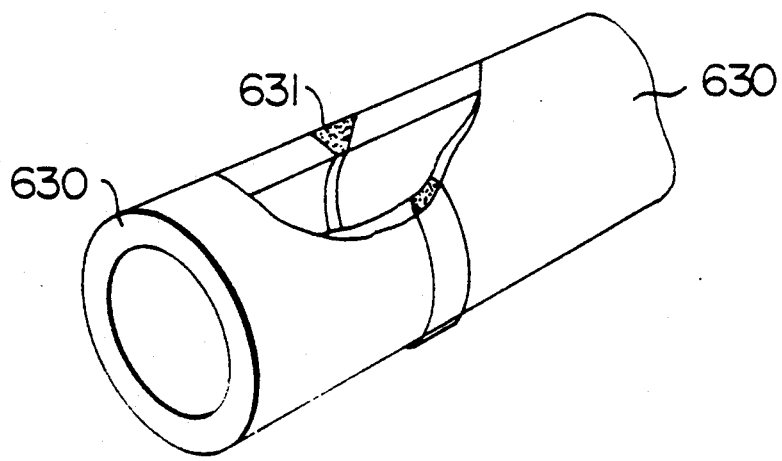
FIG. 7 is a partly sectional, perspective view of pipes of the primary piping system of the nuclear reactor shown in FIG. 5.

FIG. 7 shows part of pipes of the primary piping system 613. An austenitic stainless steel classified as SUS304 or SUS316L in JIS (Japanese Industrial Standards) is used as the material of the base metal of the pipes 630, and a welding rod of a stainless steel classified as SUS308 in JIS is used to provide a weld 631 between the pipes 630. Thus, the weld 631 between the pipes 630 has a duplex metallographic structure in which the austenite phase exists together with the ferrite phase.

Figure 8:
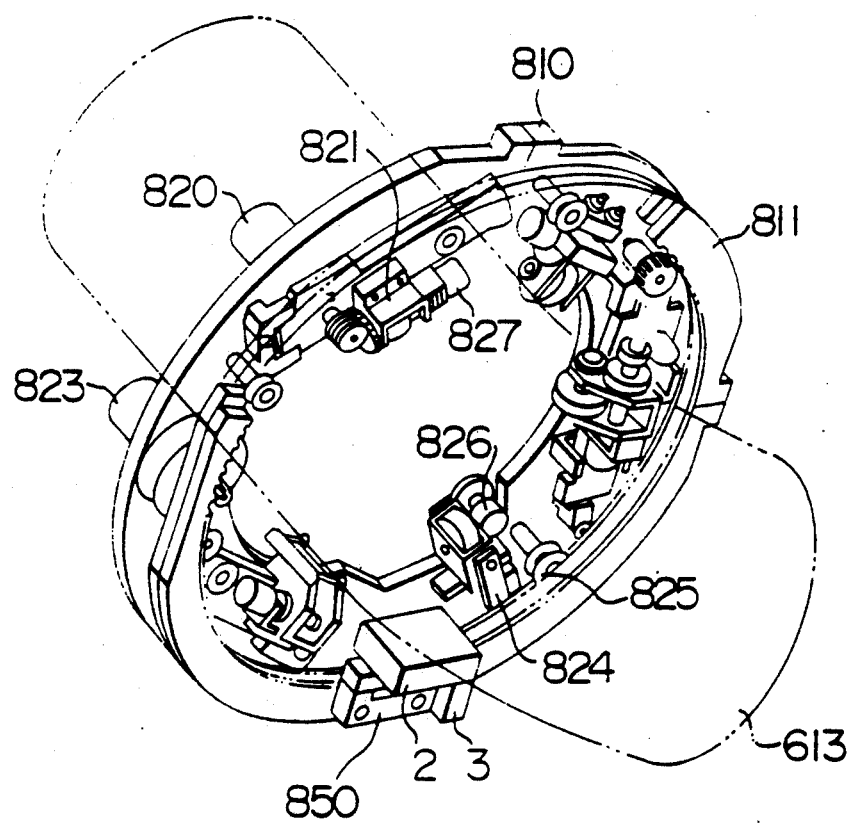
FIG. 8 a perspective view of another form of the scanning driver used for inspecting the primary piping system of the nuclear reactor shown in FIG. 5.

FIG. 8 shows the structure of another form of the scanning driver 9 used for inspecting the pipes of the primary piping system 613 of the reactor shown in FIG. 5.

Referring to FIG. 8, the scanning driver 9 includes a stationary ring 810 that can be split into halves and a rotary ring 811 rotatable in the circumferential direction of the pipes of the primary piping system 613. An axial moving mechanism including an axial drive motor 820, a gear box 821 and position detection encoders 826, 827 is mounted on the stationary ring 810. The amount of axial movement is detected by the combination of a roller 824 and the position detection encoders 826, 827, and a signal indicative of the amount of axial movement is fed back to the axial moving mechanism. The rotary ring 811 is supported on the stationary ring 810 by a plurality of pulleys 825 and is driven by a motor 823 which drives the ring 811 in the circumferential direction and has a function of detecting the circumferential position of the ring 811. A head 850 supporting the exciting system 2 and the magnetization sensor system 3 forms part of the rotary ring 811. The drive motors 820, 823, the encoders 826, 827 and the head 850 are provided with a magnetic shield so that the magnetic measurement may not be adversely affected by magnetic noise.

PRINCIPLE OF OPERATION

The principle of operation of the first embodiment of the present invention will now be described with reference to FIGS. 9, 10 and 11.

Figure 9:
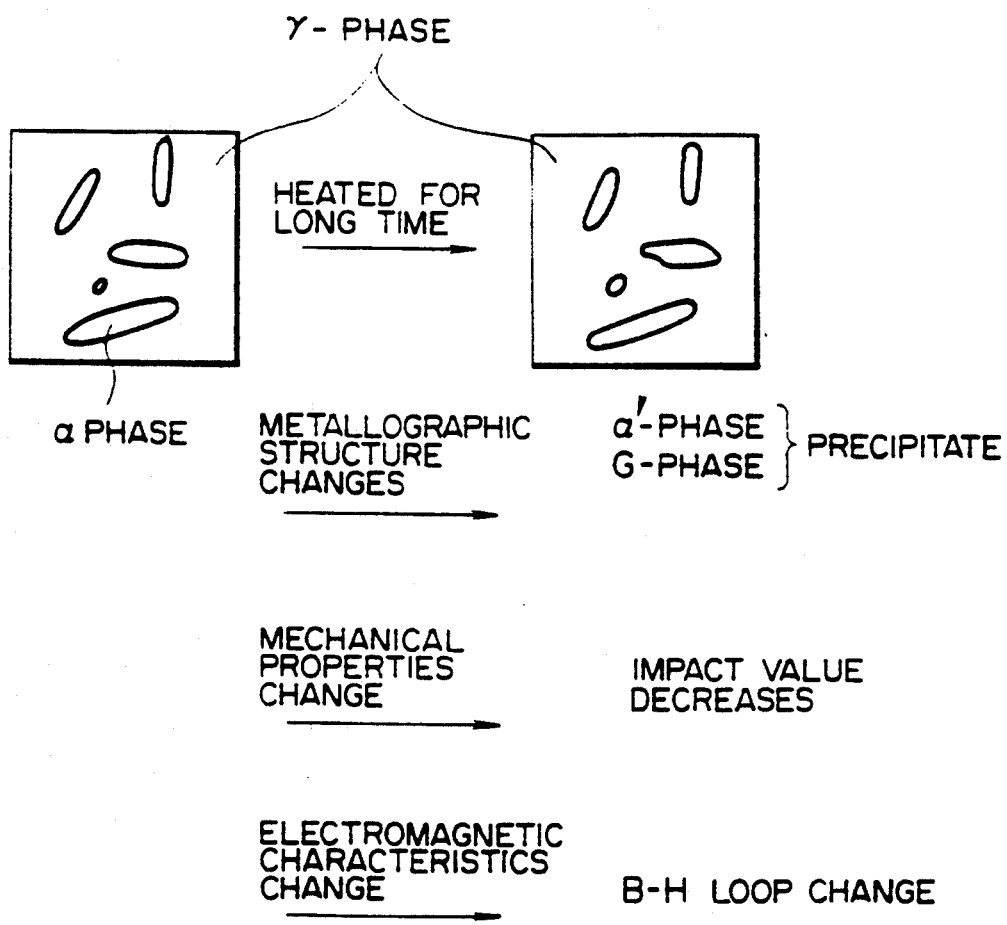
FIG. 9 shows how the metallographic structure of a metal material changes when exposed for a long period of time to a high temperature.
Figure 12:
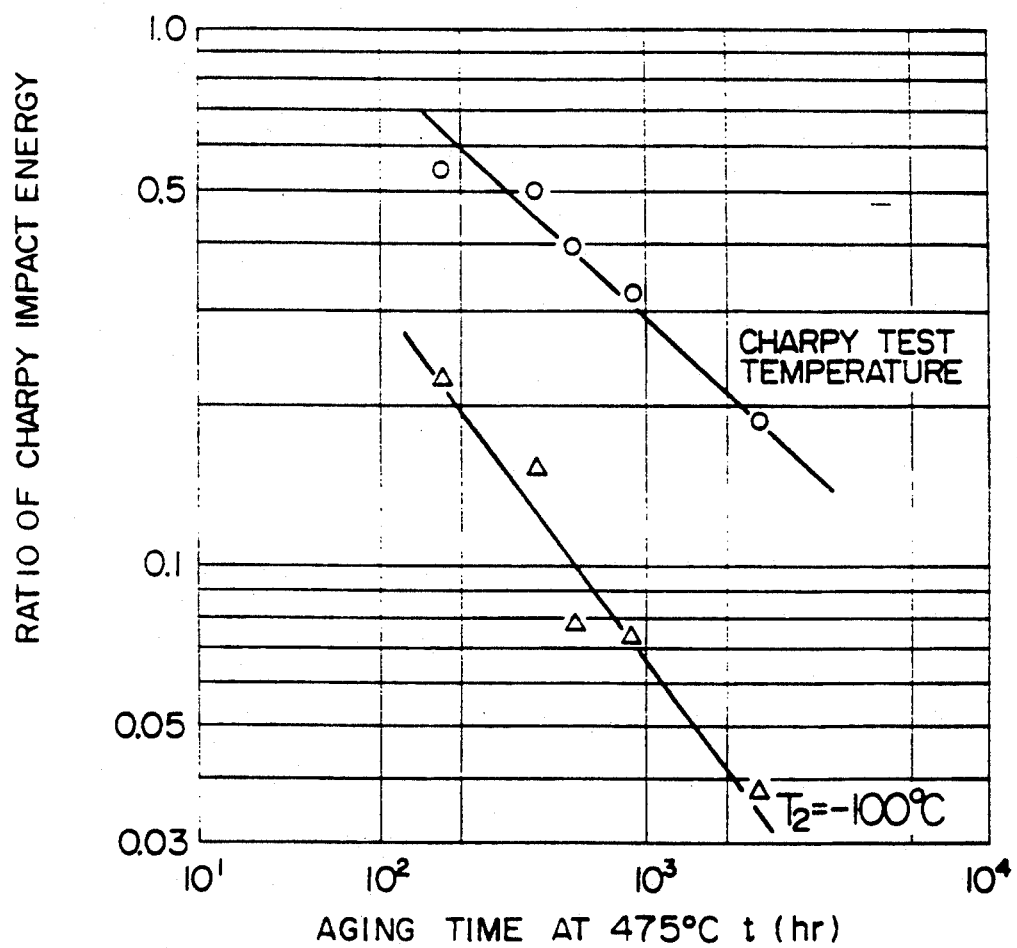
FIG. 12 is a graph showing the relation between the ratio of Charpy impact energy and the period of time of aging heat treatment of the metal material.

As shown in FIG. 9, when a metal material is used for a long period of time in an environment of a high temperature, a change generally occurs in its internal structure, resulting in a decreased mechanical strength. FIG. 12 shows the results of a Charpy impact test conducted on an aged metal material which is a ferritic stainless steel heat-treated at 475° C. It will be seen in FIG. 12 that the strength decreases with the increase in the period of aging heat treatment at a high temperature.

The inventors made researches and studies on the tendency toward embrittlement of a metal material such as a ferritic stainless steel due to heating at high temperatures. As a result of the researches and studies, the inventors found that, with the progress of aging at high temperatures, the electromagnetic characteristics such as the electrical resistivity $\rho$ and permeability $\mu$ of the metal material were subjected to a change, and the mechanical properties such as the hardness and metallographic structure of the metal material were also subjected to a change. Especially, as shown in FIGS. 10 and 11, the inventors found that a change in the tendency toward embrittlement of the metal material shown a clear correspondence with a change in the magnetization characteristic of the metal material. FIG. 10 shows the results of measurement of a magnetic hysteresis of the metal material in an as-received material, while FIG. 11 shows the results of measurement of the metal material in a high-temperature heat-treated state. The inventors found that the area of the magnetic hysteresis loop (the magnetic hysteresis loss) and the residual magnetic flux density were subjected to a change which was dependent on the degree of embrittlement of the measuring object. Thus, when such a phenomenon is utilized, the progress of the tendency toward embrittlement of a metal material, especially, a ferritic stainless steel, can be detected with high accuracy.

PROCEDURE FOR MEASUREMENT

Figure 13:
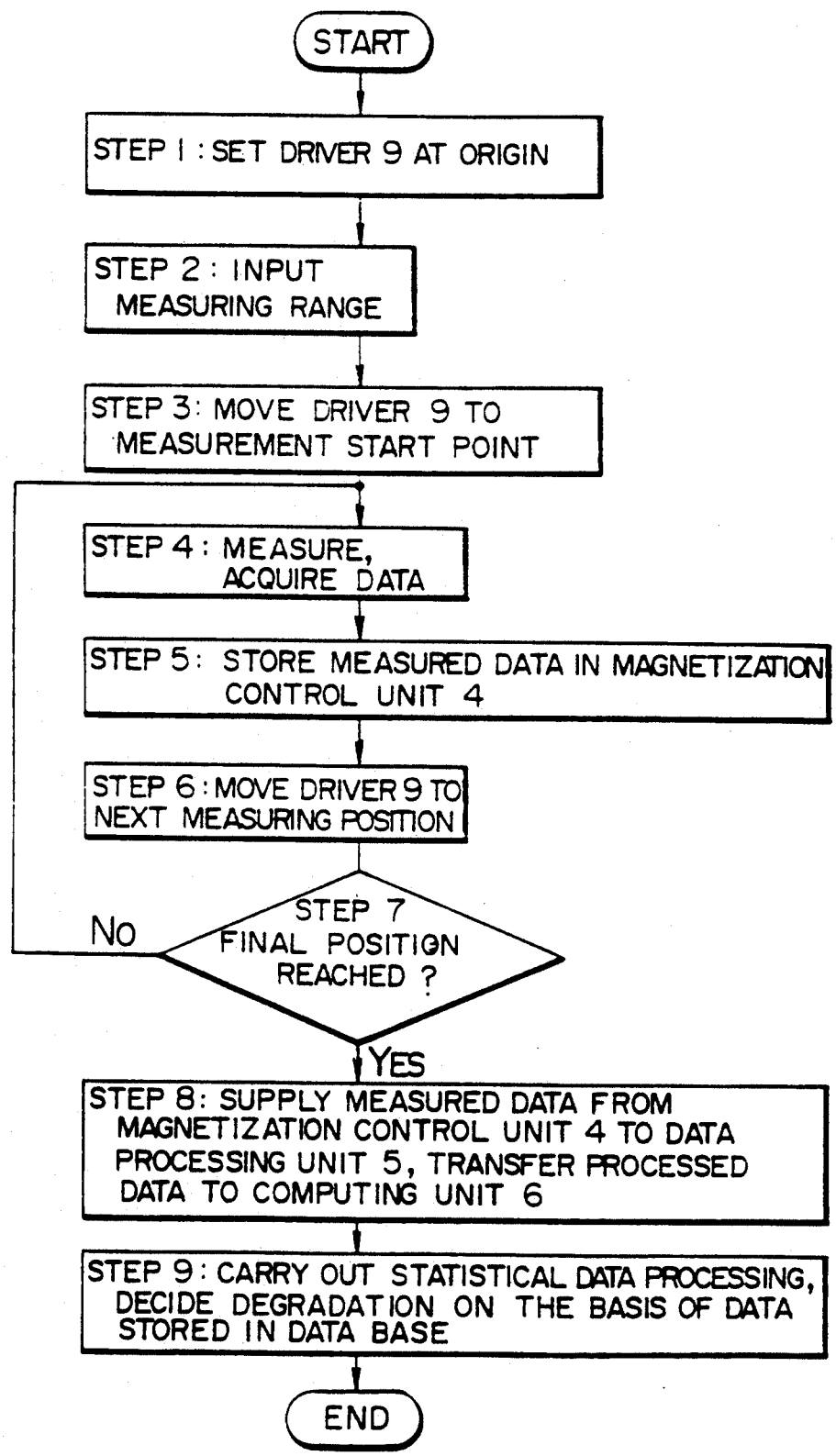
FIG. 13 is a flow chart showing the steps of measurement by the embodiment shown in FIG. 1.

One form of the procedure for measurement according to the present invention when applied to the system arrangement described with reference to FIGS. 1 to 8 will now be described with reference to a flow chart of FIG. 13.

Step 1:
First, the driver 9 is disposed opposite to the surface of the measuring object 1 such as part of the associated equipment or pipe in the nuclear reactor and is set at the origin of the measuring system.

Step 2:
The measurement or inspection range is commanded.

Step 3:
The driver 9 is moved to the starting point of measurement so that the measurement can be started.

Step 4:
The measurement is started, and the measured data at the measurement starting point is acquired.

Step 5:
The acquired data is stored in the magnetization control unit 4.

Step 6:
After completion of the measurement at the measurement starting point, the driver 9 is moved to the next measuring position.

Step 7:
Decision is made as to whether or not the driver 9 has been moved to the final position of measurement.

When the result of decision is "No", the step 7 is followed by the step 4 again, while when the result of decision is "Yes", the step 7 is followed by a step 8.

Step 8:
All the measured data are transferred from the magnetization control unit 4 to the data processing unit 5, and the measured data processed in the data processing unit 5 are transferred to the computing unit 6.

Step 9:
The measured data are processed according to a method of statistical data processing, and the data stored in the data base is based to decide the degree of aging degradation. The result of decision is supplied to an external recorder and displayed on the display unit 8.

DATA PROCESSING

The detail of the statistical data processing executed in the step 9 of FIG. 13 will now be described with reference to the drawings.

Suppose, for example, that the metal material is a ferritic stainless steel. FIG. 10 is a graph showing the magnetic flux density (B)-magnetic field intensity (H) characteristic of the stainless steel measured in an as-received material, and FIG. 11 is a graph showing the B-H characteristic of the stainless steel measured after 443 hours of heat treatment at 475° C. Thus, in the case of the ferritic stainless steel, the magnetic hysteresis loop changes from the form shown in FIG. 10 to that shown in FIG. 11 due to degradation attributable to the aging at the high temperature.

Figure 14:
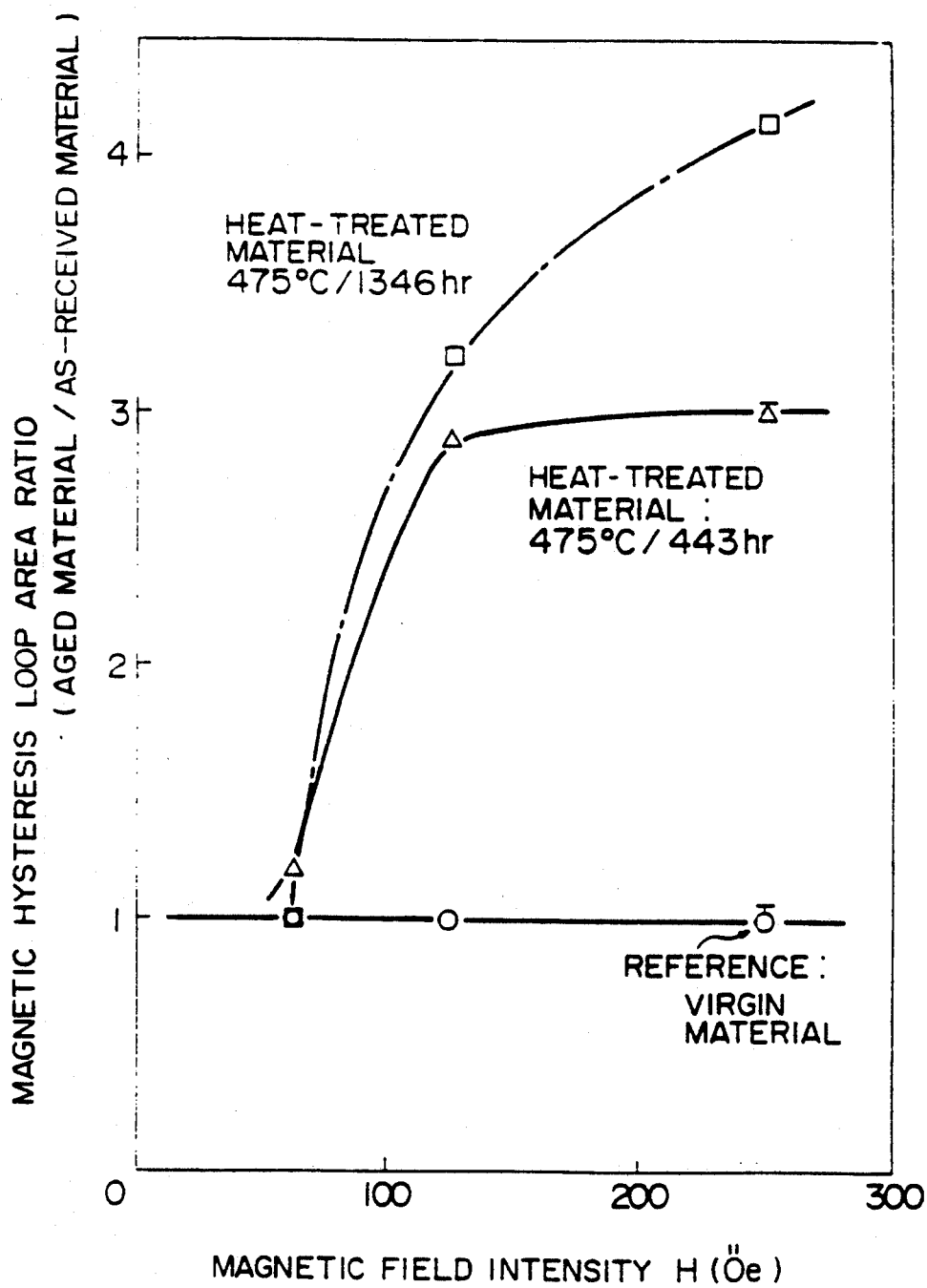
FIG. 14 is a graph showing the relation between the magnetizing force and the magnetic hysteresis loop area ratio of a metal material.
Figure 15:
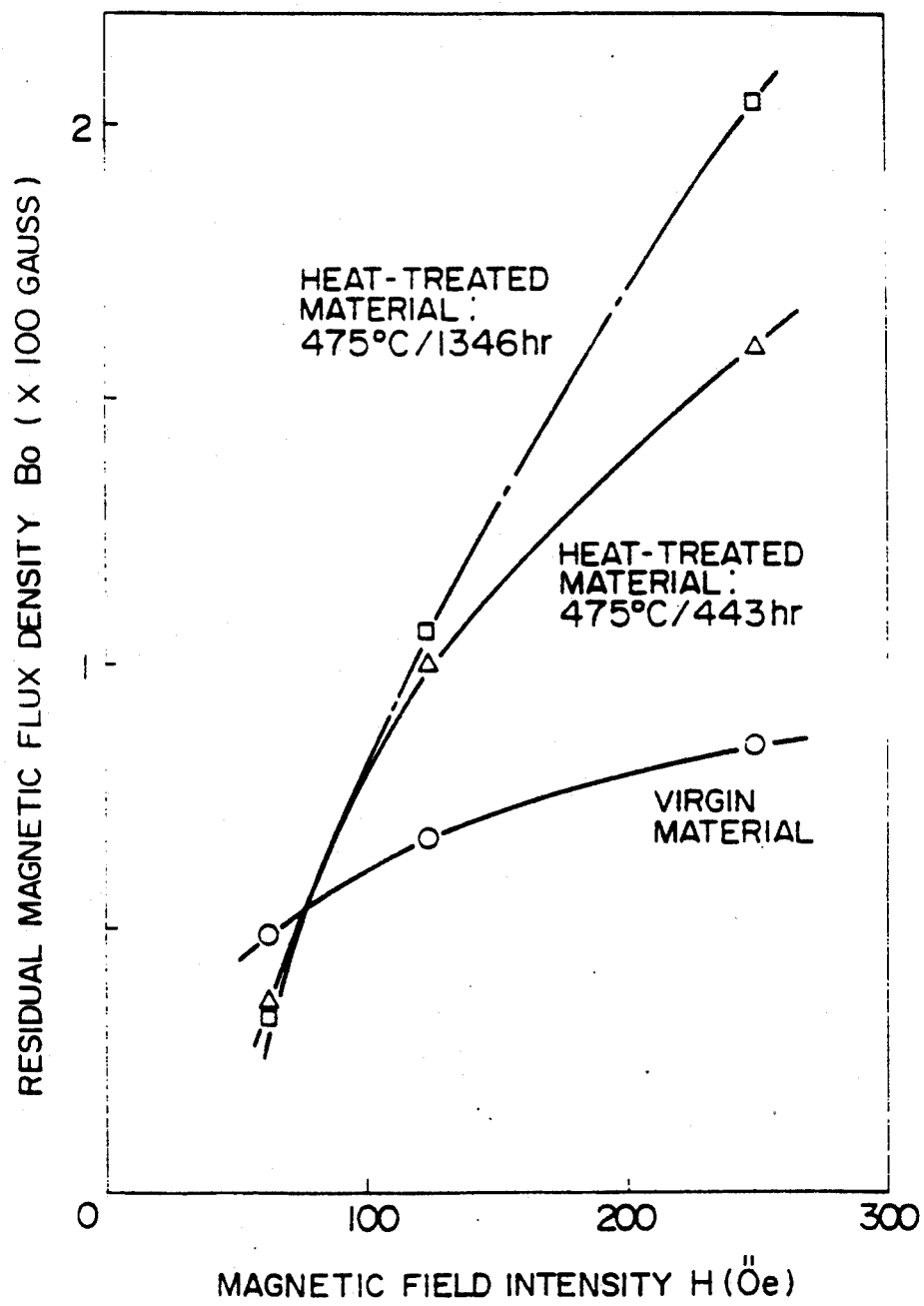
FIG. 15 is a graph showing the relation between the magnetizing force and the residual magnetic flux density of the metal material.
Figure 16:
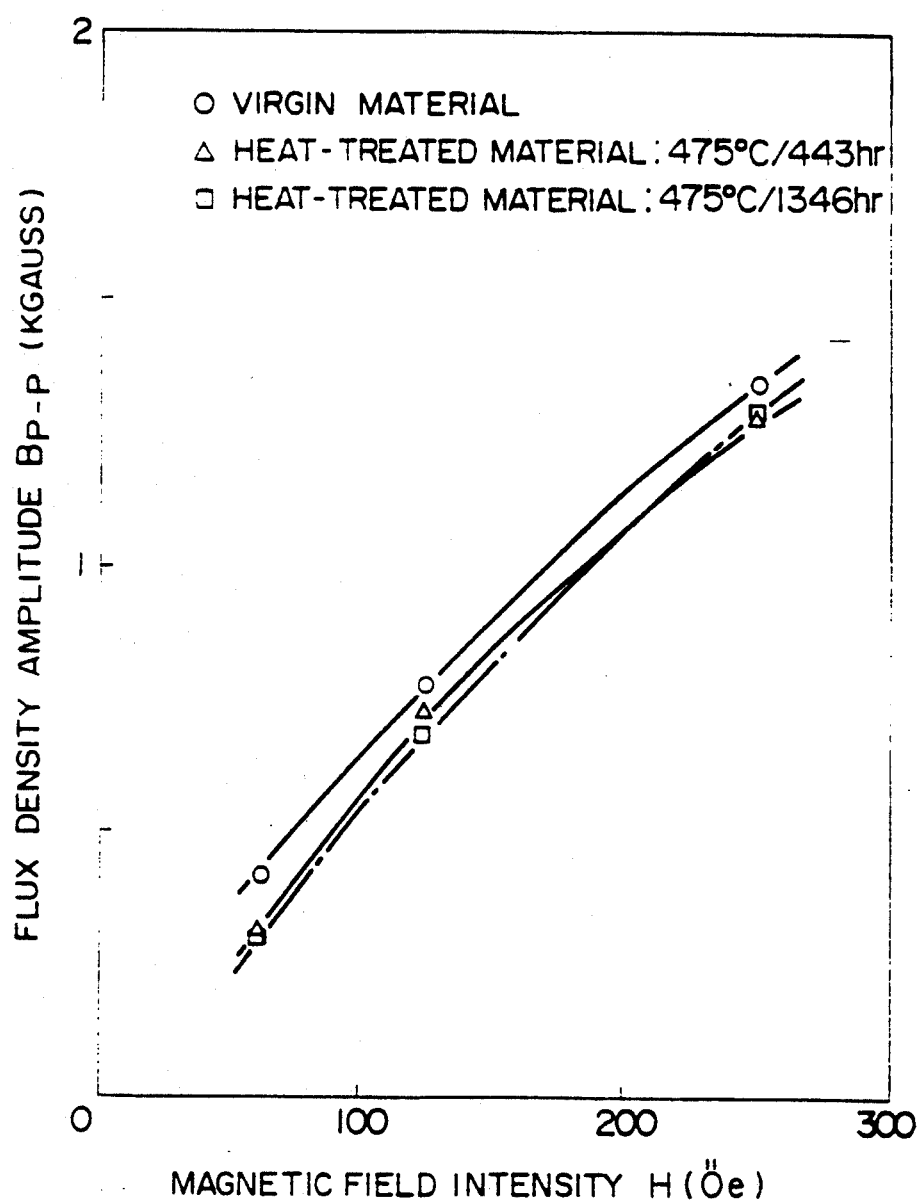
FIG. 16 is a graph showing the relation between the magnetizing force and the flux density amplitude of the metal material.

As shown in FIGS. 14 and 15, the magnetic hysteresis loop area ratio and the residual magnetic flux density of a stainless steel in its degradated state and its virgin state change depending on the magnitude of the magnetic field intensity, and a clear difference occurs between the degraded stainless steel and the virgin stainless steel when the magnetic field intensity is larger than a certain limit. However, the degree of degradation of the metal material cannot be evaluated unless the initial amount of ferrite in the metal material can be estimated. FIG. 14 is a graph showing the relation between the magnetic field intensity and the magnetic hysteresis loop area ratio, and FIG. 15 is a graph showing the relation between the magnetic field intensity and the residual magnetic flux density. In FIGS. 14 and 15, the magnetization characteristics of the virgin stainless steel are compared with those of the heat-treated stainless steel. On the other hand, FIG. 16 shows that the relation between the maximum magnetic flux density and the magnetic flux intensity does not appreciably change depending on whether the stainless steel is not heat-treated or is heat-treated and aged at a high temperature. This maximum magnetic flux density is determined by the initial amount of ferrite in the stainless steel. FIG. 16 is a graph showing the relation between the magnetic flux intensity and the amplitude of the magnetic flux density.

Figure 17:
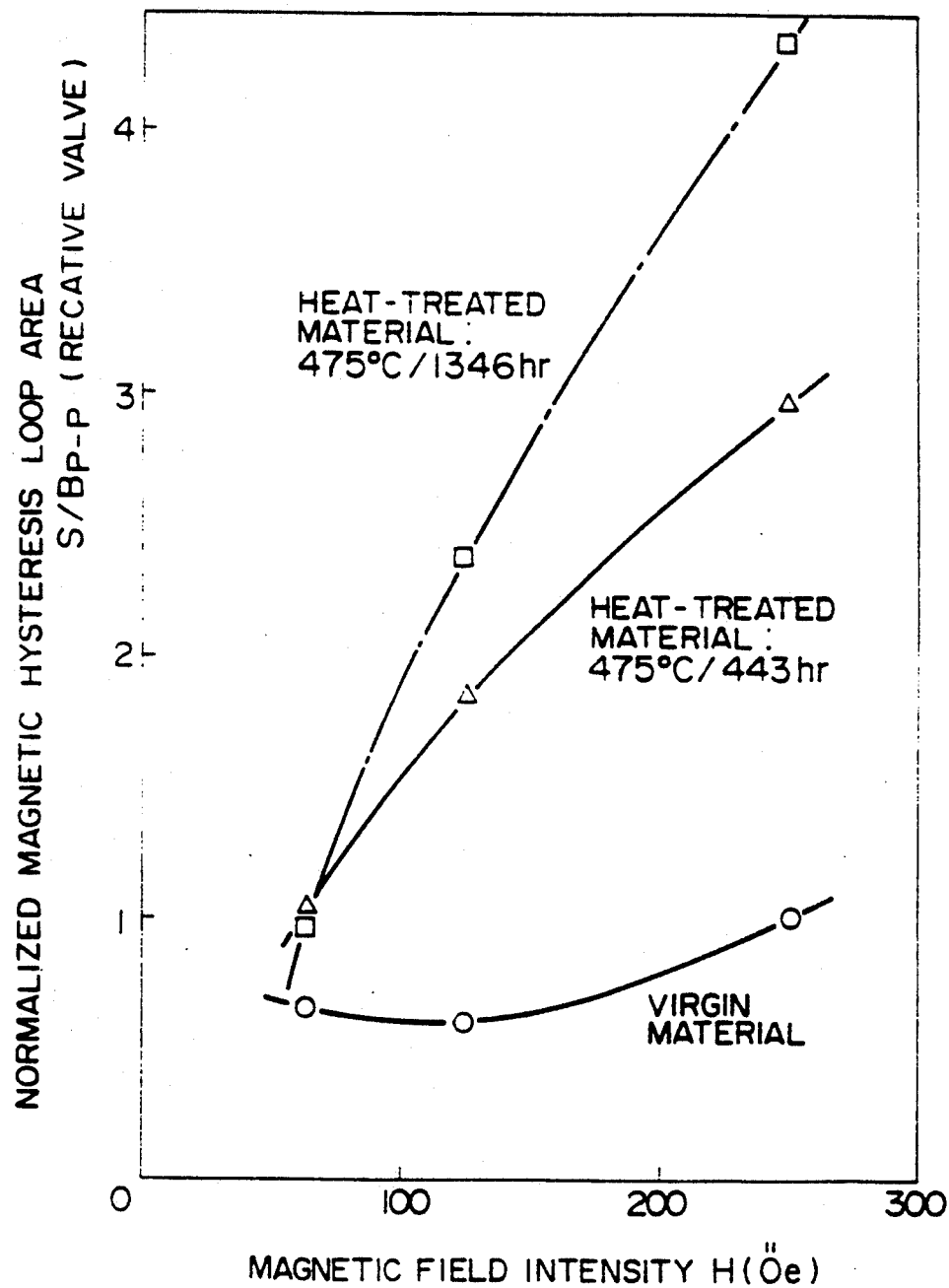
FIG. 17 is a graph showing the relation between the magnetizing force and the normalized magnetic hysteresis loop area of the metal material.
Figure 18:
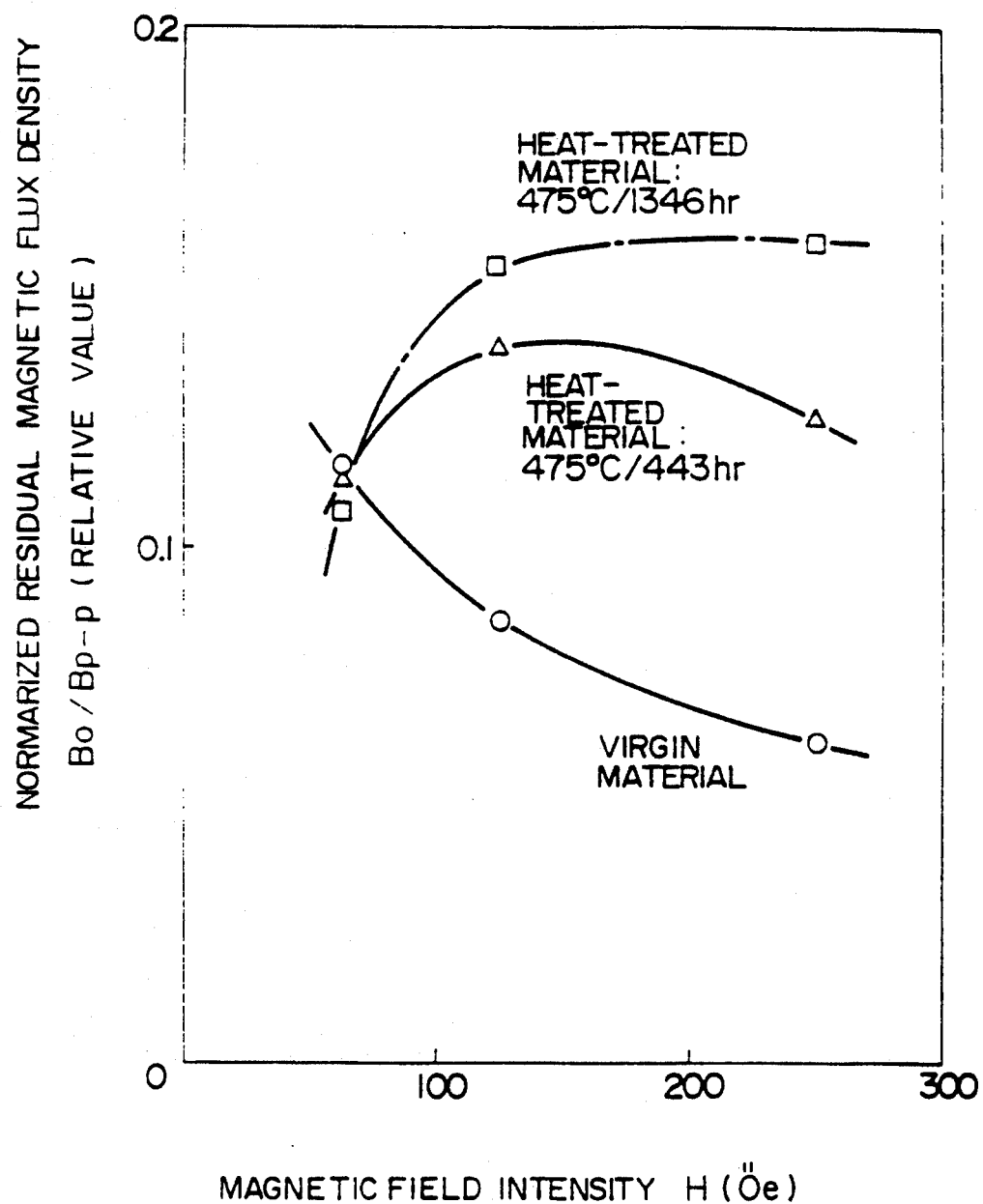
FIG. 18 is a graph showing the relation between the magnetizing force and the normalized residual flux density of the metal material when the magnetic flux density is fixed.

FIG. 17 is a graph showing the relation between the magnetic flux intensity and the normalized magnetic hysteresis loop, and FIG. 18 is a graph showing the relation between the magnetic flux intensity and the normalized residual magnetic flux density. In FIGS. 16, 17 and 18, the magnetization characteristics of the virgin stainless steel are compared with those of the heat-treated stainless steel. It will be seen in FIGS. 16 and 17 that, for the purpose of correction of variations of the initial amount of ferrite in the stainless steel, it is effective to evaluate the degree of degradation of the metal material on the basis of the normalized area ratio between the magnetic hysteresis loops normalized by the maximum magnetic flux density or on the basis of the normalized residual magnetic flux: density.

Figure 19:
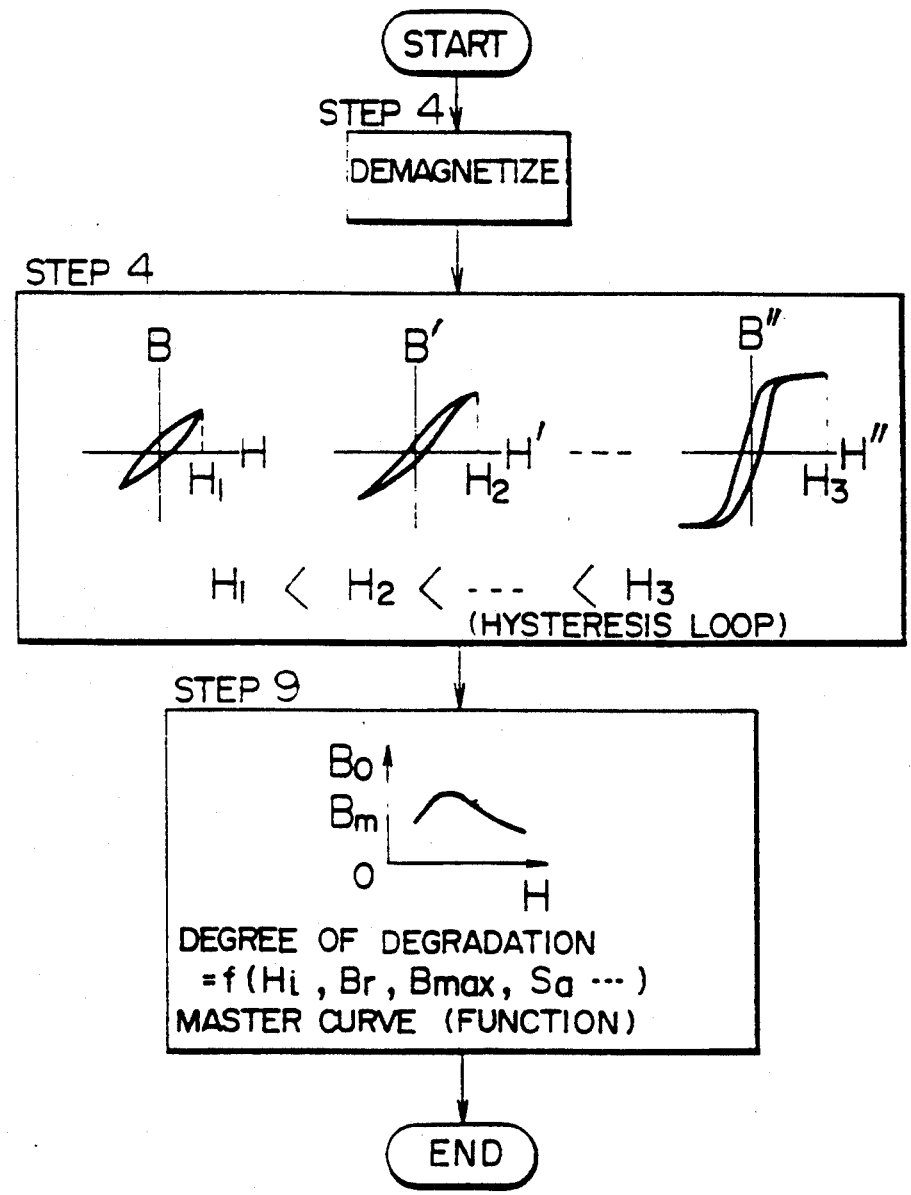
FIG. 19 is a flow chart showing one form of the steps for decision of degradation by the method according to the present invention.

Thus, in the step 4 of measurement to acquire data, it is preferable to demagnetize the measuring object 1 and detect magnetic hysteresis loops at various levels $H_1$, $H_2$, ---, $H_3$ ($H_1 < H_2$ --- $< H_3$) of the magnetic field intensity to acquire necessary data as shown in FIG. 19. Then, in the step 9 of data processing, the degree of degradation of the measuring object 1 is decided on the basis of a previously determined master curve or a previously computed evaluation function as shown in FIG. 19.

Thus, it is preferable that magnetic hysteresis loops of the material of the specific measuring object are detected by continuously or discretely changing the magnetic field intensity, and the data of the normalized magnetic hysteresis loop area and the data of the normalized magnetic flux density shown in FIGS. 17 and 18 are used to prepare a calibration curve. When such a calibration curve is prepared for each of many kinds of stainless steels to provide a data base, and measured data is compared with corresponding data of the data base, the degree of degradation of the measuring object can be estimated without requiring initial data of the measuring object.

SECOND METHOD OF DECISION

A second form of the method of decision comprises magnetizing a degradated metal material by a predetermined magnetic field intensity and estimating the degree of degradation on the basis of the value detected at that time.

Figure 20:
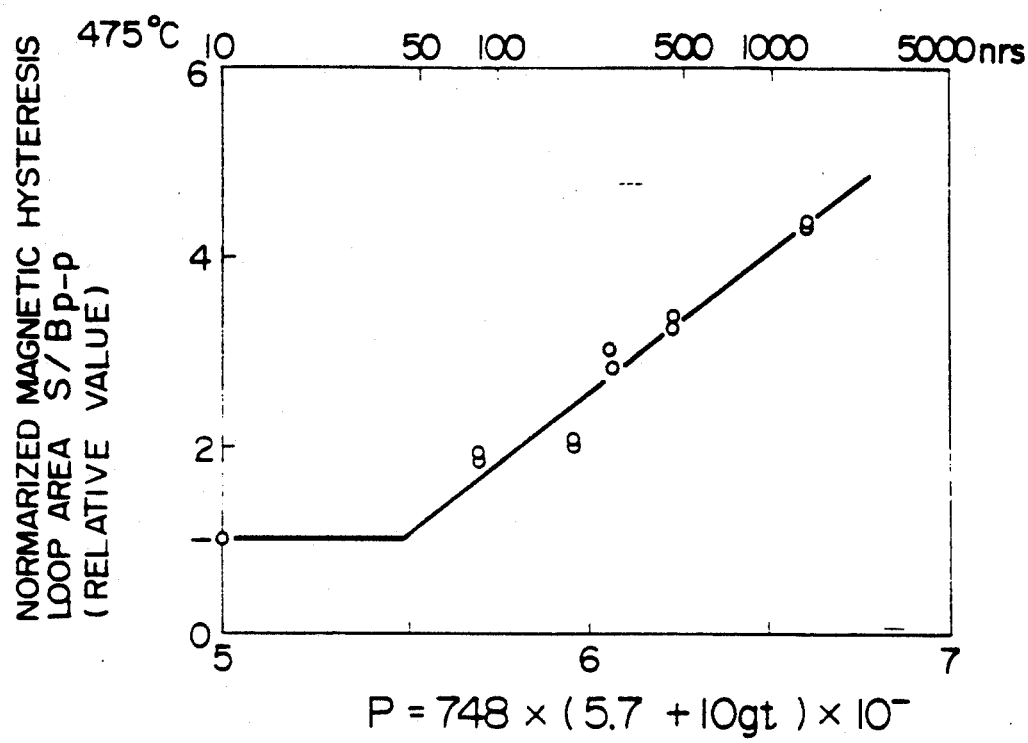
FIG. 20 is a graph showing the relation between the normalized magnetic hysteresis loop area and a degradation parameter of a metal material.
Figure 21:
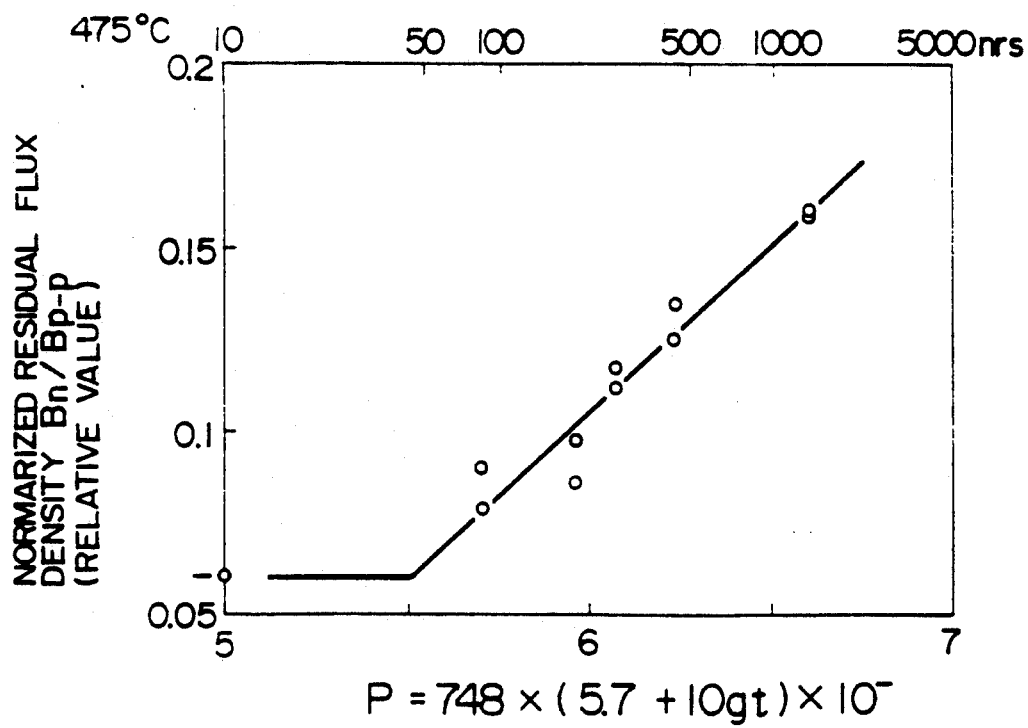
FIG. 21 is a graph showing the relation between the normalized residual flux density and the degradation parameter of the metal material.

As shown in FIGS. 14 and 15, the magnetic hysteresis loop area ratio and the residual magnetic flux density change depending on the magnitude of the magnetic flux intensity, and a clear difference appears between a degradated metal material and an as-received virgin metal material when the magnetic field intensity exceeds a certain limit. Therefore, the magnetic field intensity is set at a value suitable for detection of degradation of a metal material, and the magnetic hysteresis loop of the metal material is measured. Graphs as shown in FIGS. 20 and 21 are obtained when the parameters such as the magnetic hysteresis loop area, residual magnetic flux density and maximum magnetic flux density of the metal material are plotted relative to a degradation parameter indicative of the degree of degradation. (This degradation parameter is, for example, the value P in the Larson-Miller's rule.)

Figure 22:
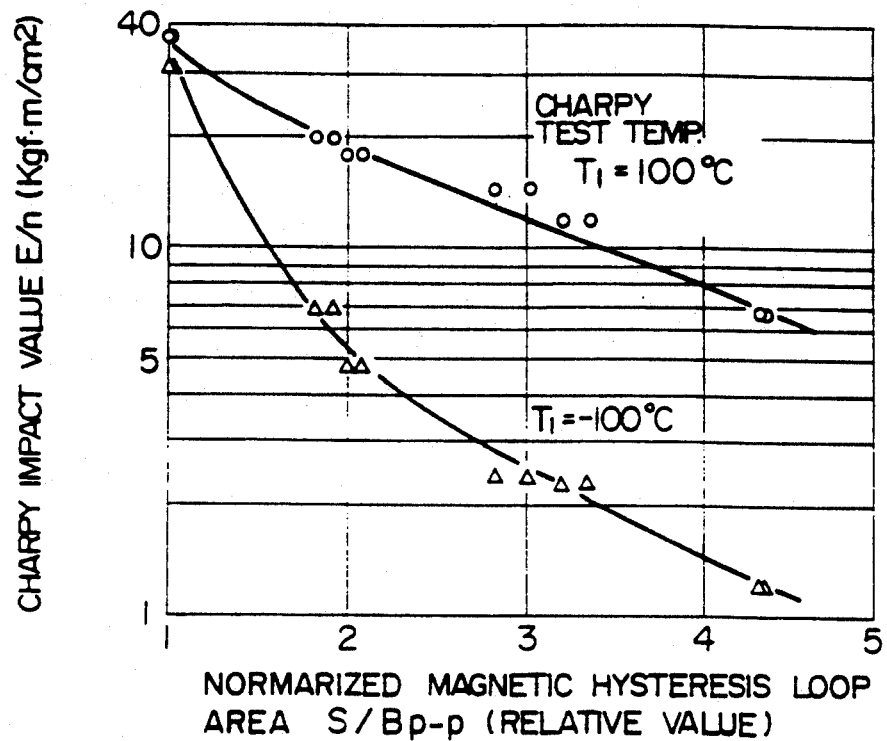
FIG. 22 is a graph showing the relation between the normalized magnetic hysteresis loop area and the Charpy impact value of the metal material.
Figure 23:
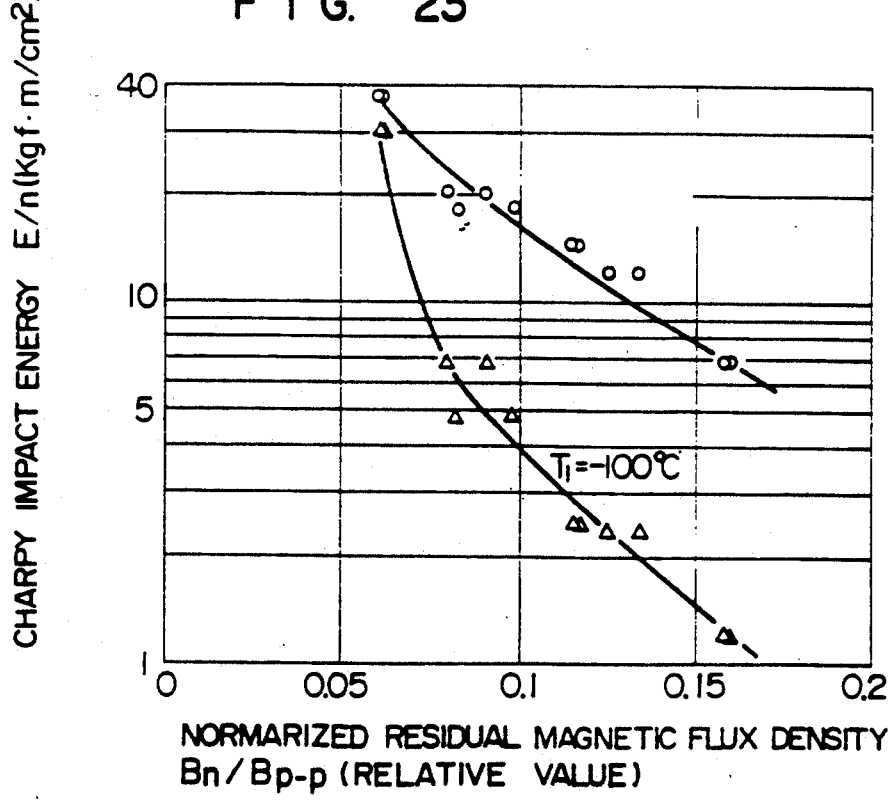
FIG. 23 is a graph showing the relation between the normalized residual flux density and the Charpy impact value of the metal material.

That is, on the basis of the measured data of the magnetic hysteresis loop area, residual magnetic flux density and maximum magnetic flux density of the metal material, the value of the degradation parameter, that is, the value P is determined so that the degree of degradation of the metal material can be estimated. Therefore, the degree of degradation of the metal material can be estimated when the data shown in FIGS. 20 and 21 are used to provide a data base. For example, the metal material may be previously subjected to a Charpy impact test, and the Charpy impact energy or fracture toughness value of the metal material may be used as the degradation parameter of the metal material. When such data shown in FIGS. 22 and 23 are used to provide part of the data base, the breaking or fracture strength of the metal material can also be estimated.

THIRD METHOD OF DECISION

Figure 24:
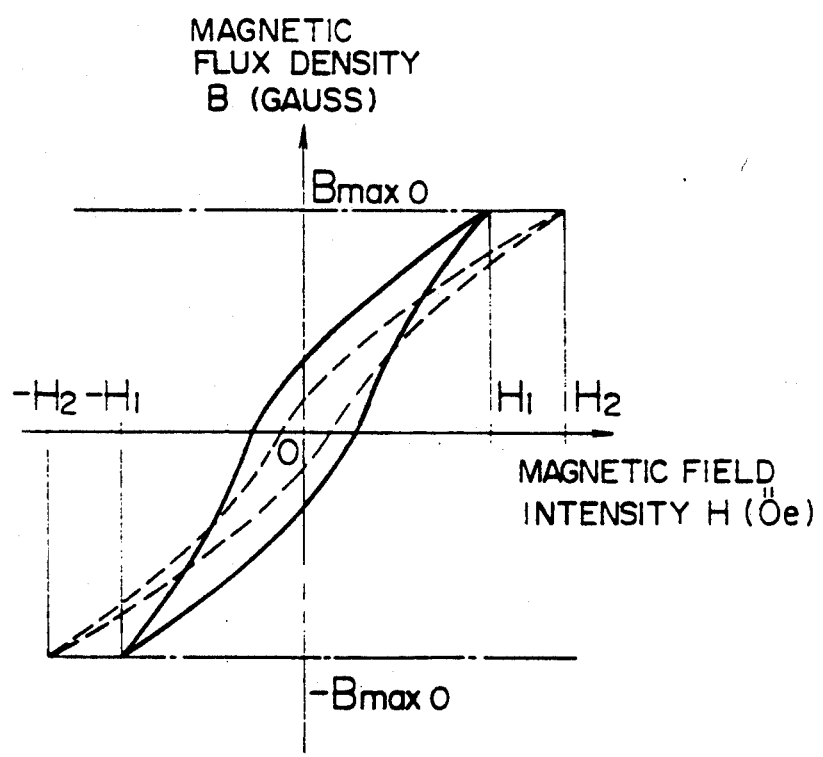
FIG. 24 is a graph showing the relation between the magnetizing force and the magnetic hysteresis loop of the metal material when the magnetic flux density is fixed.

In the second method of decision described above, the magnetic hysteresis loop of a metal material is measured while setting the magnetic field intensity at a predetermined value. According to a third method, the magnetic hysteresis loop of a metal material is measured while setting the magnetic flux density at a predetermined value as shown in FIG. 24. In the third method, the magnetic flux density used for exciting the metal material is fixed so as to control the magnetic field intensity with high accuracy during measurement of the magnetic hysteresis loop. Therefore, the reproducibility and accuracy of the measured data can be easily improved.

FOURTH METHOD OF DECISION

According to a fourth method of decision, the degree of degradation of a metal material is estimated on the basis of the pattern of the magnetic hysteresis loop of the metal material.

Figure 10:
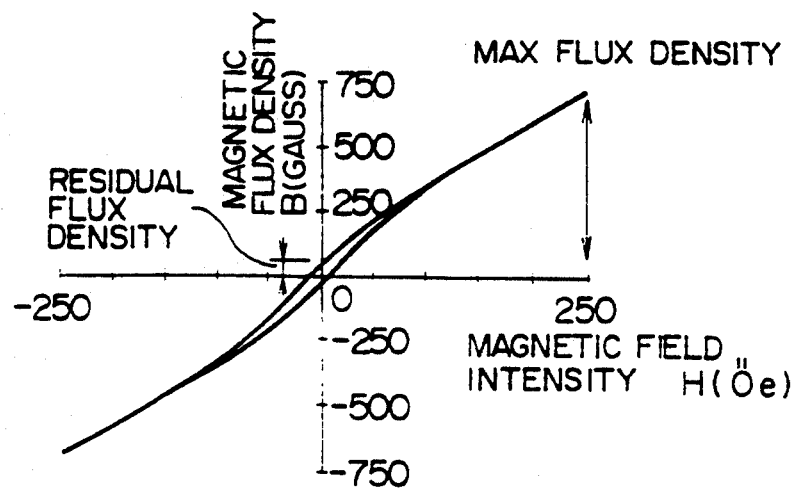
FIG. 10 is a graph showing the relation between the magnetic flux density and the magnetizing force of a metal material in an unused virgin state.
Figure 11:
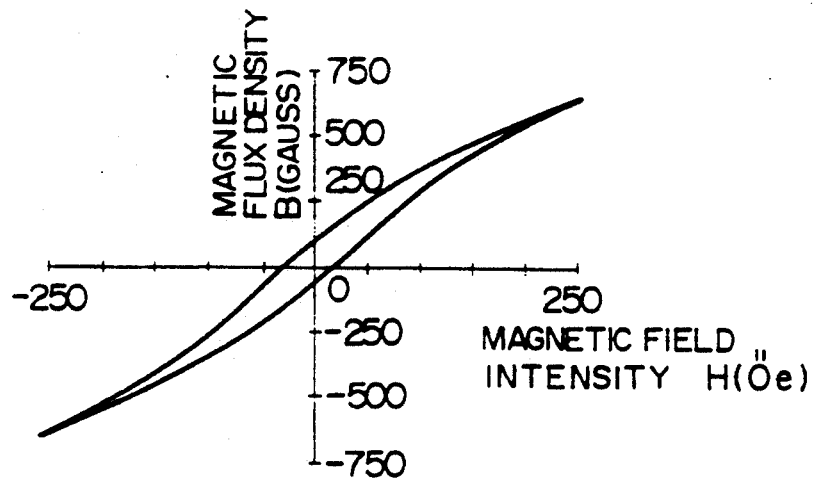
FIG. 11 is a graph showing the relation between the magnetic flux density and the magnetizing force of the metal material after having been subjected to heat treatment.
Figure 25:
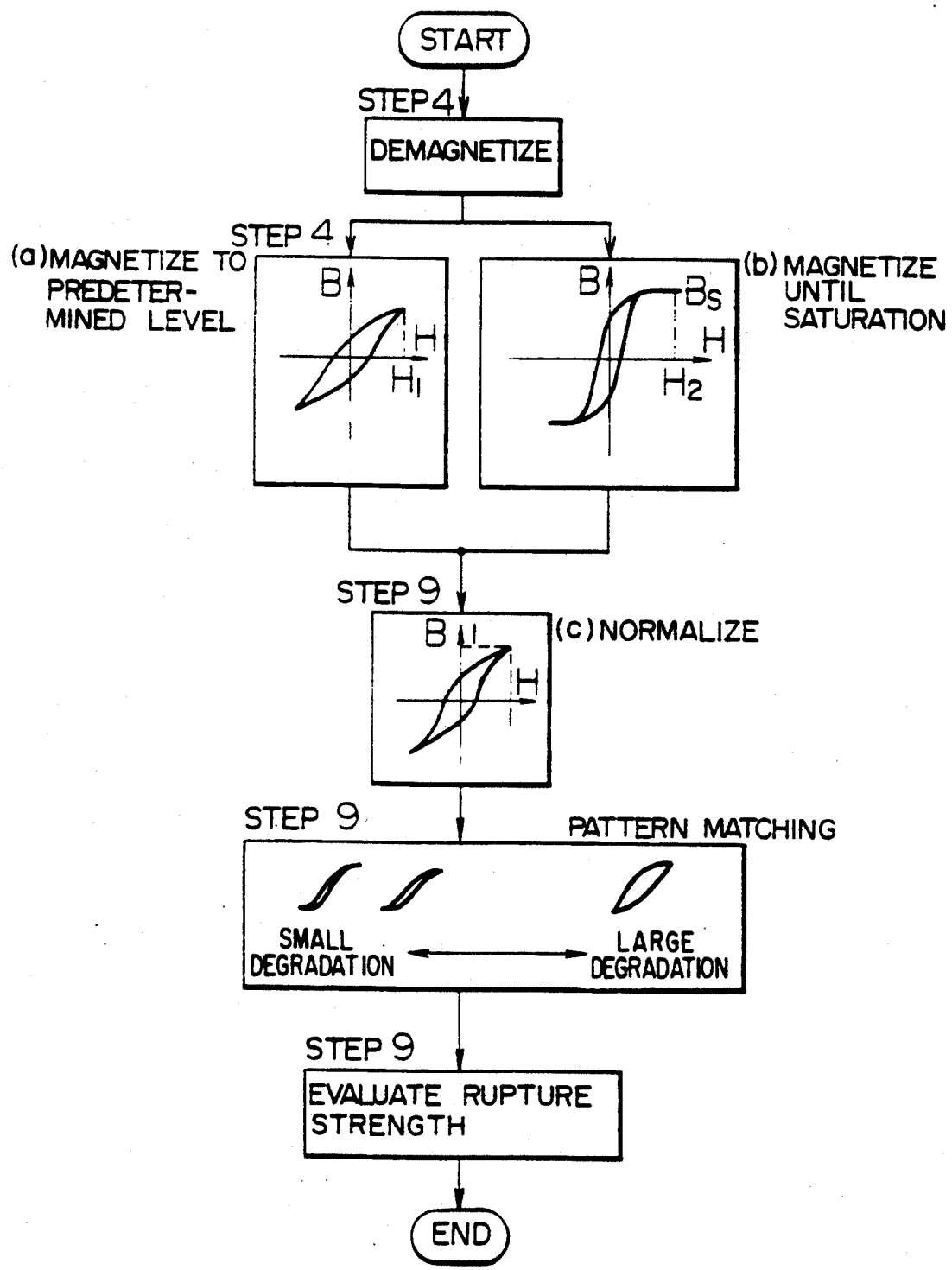
FIG. 25 is a flow chart showing the steps for estimating the degree of degradation of a metal material on the basis of the pattern of the magnetic hysteresis loop according to another embodiment of the method of the present invention.

As seen in FIGS. 10 and 11, the pattern of the magnetic hysteresis loop of a metal material shows a correspondence with the degree of degradation of the metal material. FIG. 25 is a flow chart showing how the degree of degradation of a metal material is estimated on the basis of the pattern of the magnetic hysteresis loop.

In the step 4 of measurement and data acquisition in the flow chart of FIG. 25, a measuring object is demagnetized, and necessary data is acquired from a magnetic hysteresis loop measured by magnetizing the measuring object to a state of predetermined magnetization or by magnetizing the measuring object to a state of magnetic saturation. In the step 9 of acquired data processing, the magnetic hysteresis loop is normalized, and the pattern of the normalized magnetic hysteresis loop is used for pattern matching with previously determined, reference hysteresis loop patterns stored in a data base. As a result of the pattern matching, the magnetic hysteresis loop most analogous to the pattern of the measured magnetic hysteresis loop is selected from the data base, and the degree of degradation or fracture strength of the measuring object is estimated on the basis of the degree of degradation of the selected magnetic hysteresis loop.

FIFTH METHOD OF DECISION

Figure 26:
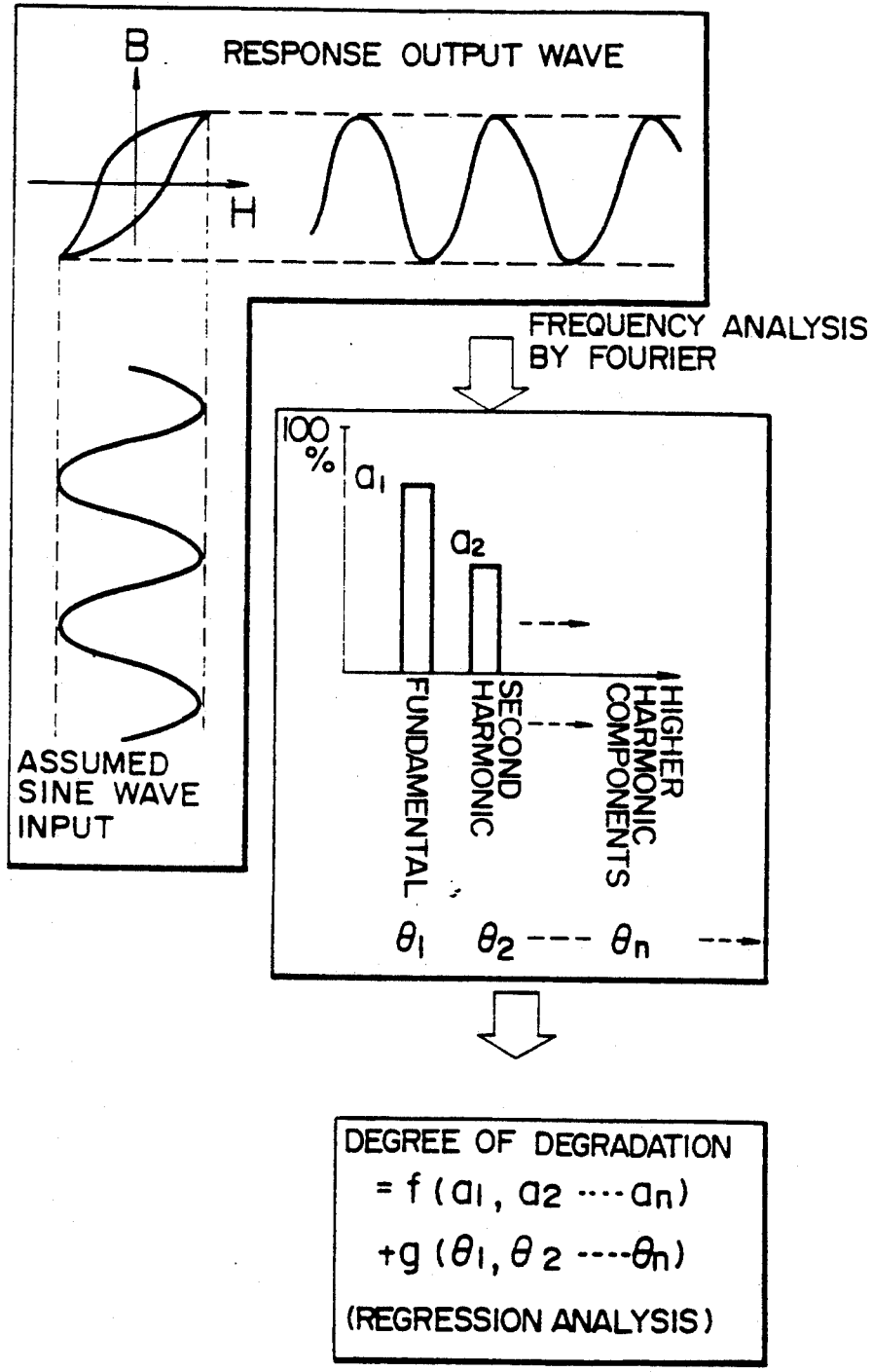
FIG. 26 is also a flow chart showing the steps for deciding the degree of degradation of a metal material by means of the Fourier transformation of data of the magnetic hysteresis loop of the metal material.

FIG. 26 shows a fifth method of decision. In the step 9 of data processing in the flow chart of FIG. 13, the measured magnetic hysteresis loop is used to detect the output waveform of the magnetic flux density when a sine wave input is applied to generate the magnetic field intensity, and an output waveform distortion of the magnetic flux density is computed by the Fourier transformation. Then, on the basis of the magnitude and phase difference of individual higher harmonic components, the degree of degradation of the metal material is detected from the data base storing necessary data computed according to a technique of statistical data processing such as a regression analysis.

GENERAL SYSTEM ARRANGEMENT OF SECOND EMBODIMENT

Figure 27:
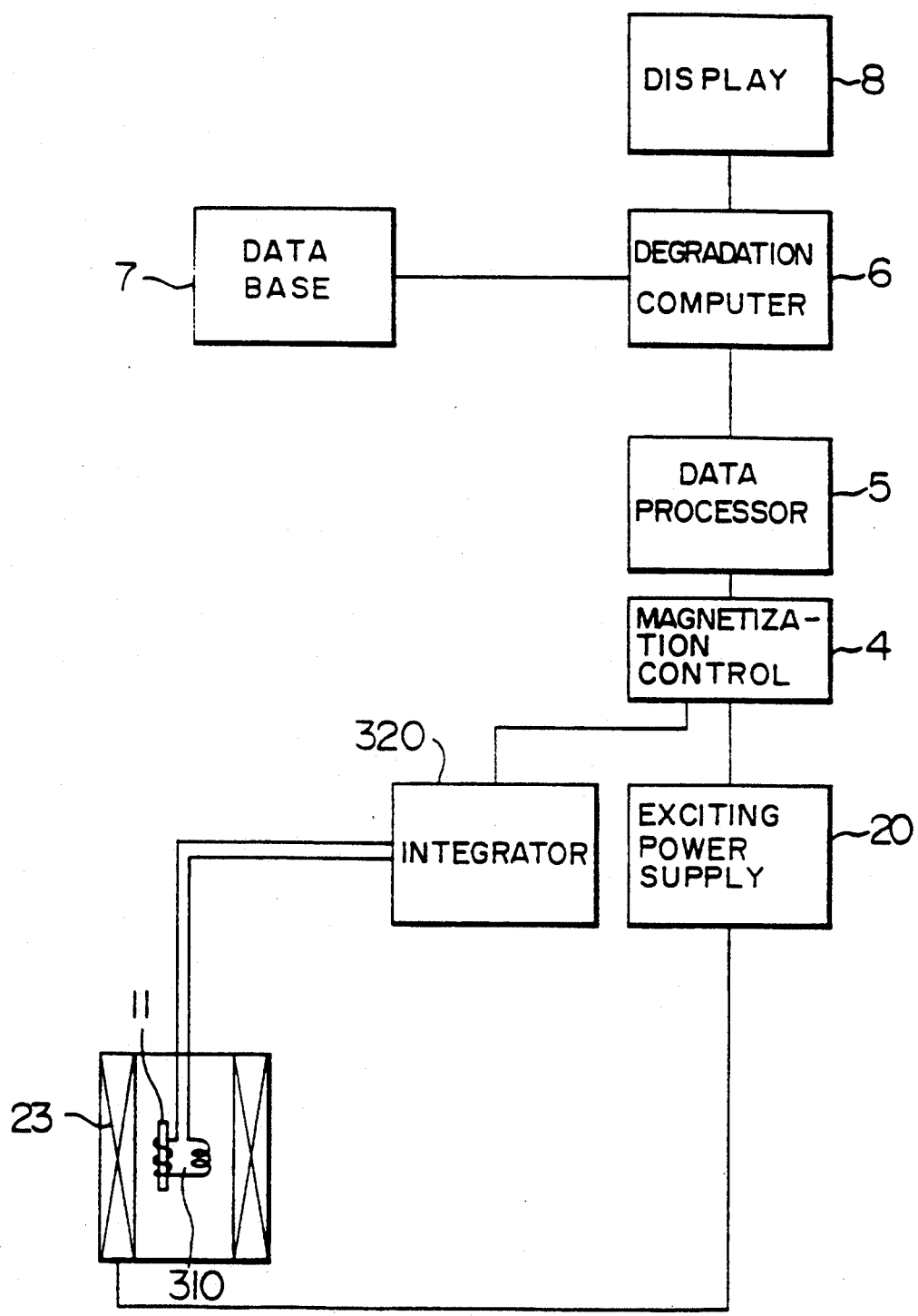
FIG. 27 is a general block system diagram of a second embodiment of the degradation detecting apparatus according to the present invention.

FIG. 27 shows a second embodiment of the present invention. This second embodiment is a modification of the first embodiment shown in FIG. 1, and the measuring object can be acquired in the form of a small sample 11. This small sample 11 is inserted into the exciting coil 23 connected to an exciting power supply unit 20. A differential detection coil 310 is wound around the sample 11, and the output of the coil 310 is integrated by an integrator 320 which computes the magnetic flux density. The manner of data processing in this second embodiment is similar to that in the first embodiment.

THIRD EMBODIMENT UTILIZING SUPERCONDUCTING SYSTEM

Figure 28:
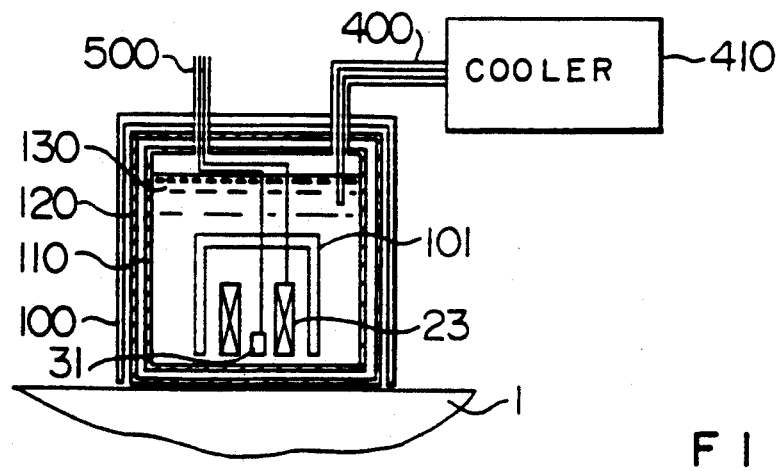
FIGS. 28, 29 and 30 are schematic sectional views of part of a third embodiment of the present invention and its modifications utilizing a superconducting system respectively.
Figure 29:
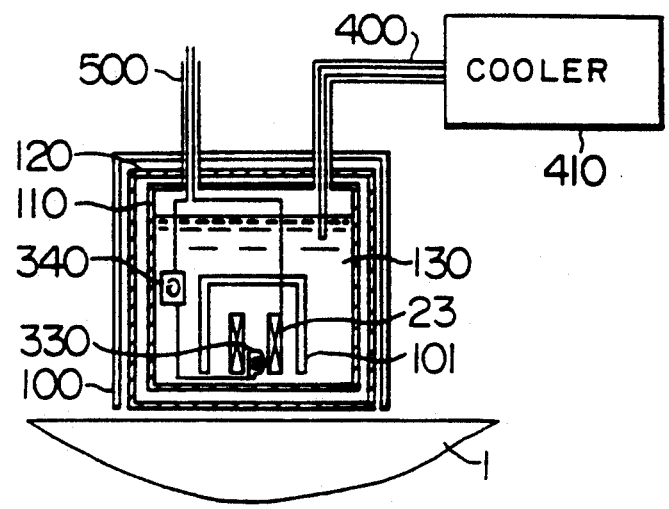
Figure 30:
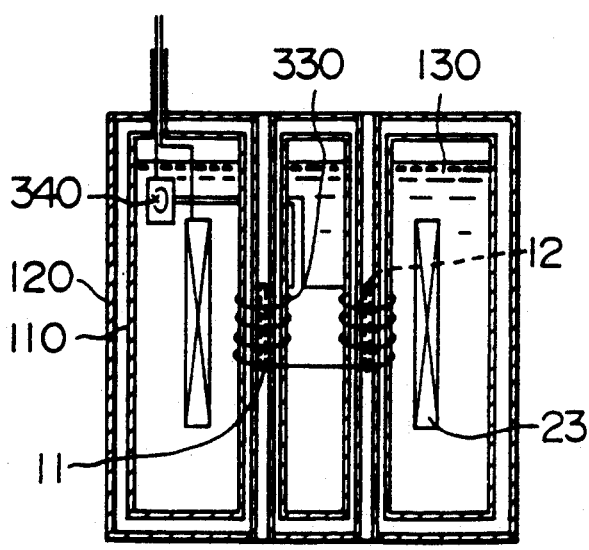

FIGS. 28, 29 and 30 show part of a third embodiment and its modifications respectively in each of which a superconducting system is used to replace the exciting system 2 and magnetization sensor system 3 shown in FIG. 1.

In FIG. 28 showing a partial modification of the first embodiment, a superconducting system is used for the exciting coil 23 so as to magnetize a measuring object 1 by applying a strong magnetic field thereby improving the accuracy of degradation detection. Referring to FIG. 28, a sensor container 110 of a non-magnetic material filled with a coolant 130 is disposed opposite to the surface of the measuring object 1, and a superconducting exciting coil 23 is installed in the sensor container 110, so that the superconducting exciting coil 23 can be maintained in its superconducting state. The magnetization sensor 31 which can operate at low temperatures is located at the center of the superconducting exciting coil 23. The sensor container 110 is thermally insulated from the atmosphere by a thermal insulating member 120. The coolant 130 is recirculated by a conduit 400 to an external cooling device 410 to be cooled. Magnetic shields 100 and 101 are disposed outside the sensor container 110 and exciting coil 23 respectively so as to optimize the external magnetic field and exciting magnetic field. The exciting coil 23 and magnetization sensor 31 are connected by connection cables 500 to the magnetization control unit 4.

According to this third embodiment, a strong magnetic field can be produced by the exciting coil of small size, so that diagnostic evaluation of the degree of degradation of a localized area can be attained.

FIG. 29 shows a modification of the embodiment shown in FIG. 28. In FIG. 29, the magnetization sensor 31 shown in FIG. 28 is replaced by a superconducting quantum interference device (SQUID) 340 having a high detection sensitivity. A pickup coil 330 for the superconducting quantum interference device 340 is disposed at the center of the exciting coil 23, and the superconducting quantum interference device 340 is disposed outside the magnetic shield 101 to make magnetic measurement.

According to the embodiment shown in FIG. 29, the magnetic field can be detected with a high sensitivity, so that the efficiency of detection of degradation of a metal material can be remarkably improved.

FIG. 30 shows a modification of the embodiment shown in FIG. 29, and the measuring object 1 can be acquired in the form of a small sample 11. The superconducting exciting coil 23 is placed in the coil container 110 of a non-magnetic material filled with the coolant 130 so that the coil 23 can be maintained in its superconducting state. The coil container 110 is thermally insulated from the ambient atmosphere by the thermal insulating member 120. The coil container 110 containing the superconducting exciting coil 23 is formed at its central area with a pair of spaced holes, so that the sample 11 and a reference sample 12 can be inserted into the respective holes from the outside. The superconducting exciting coil 23 establishes a uniform magnetic field in the zone where the samples 11 and 12 are placed. The differential pickup coil 330 associated with the superconducting quantum interference device 340 is wound around the acquired sample 11 and reference sample 12 in the two holes, and the superconducting quantum interference device 340, which is magnetically shielded, makes magnetic measurement. Thus, the difference between the magnetization characteristics of the acquired sample 11 and reference sample 12 can be detected.

According to the embodiment shown in FIG. 30, a change in the magnetization characteristic of the metal material can be detected with high accuracy, so that a distortion of the magnetic field can be detected with high accuracy thereby greatly improving the accuracy of evaluation of the degree of degradation of the metal material.

SYSTEM ARRANGEMENT OF FOURTH EMBODIMENT

Figure 31:
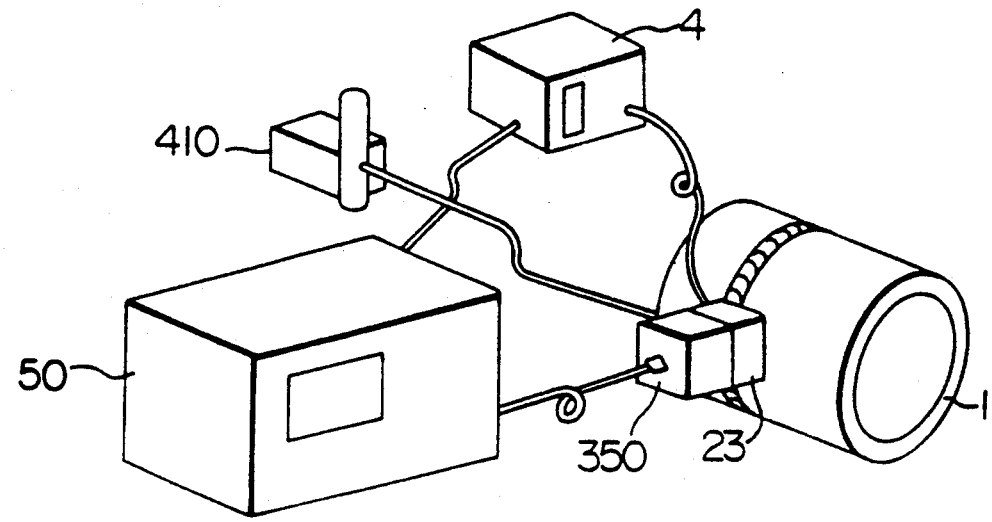
FIG. 31 is a schematic perspective view of a fourth embodiment of the present invention.

FIG. 31 shows a basic system arrangement employed for putting into practical use a fourth embodiment of the apparatus of the present invention for inspecting degradation of a metal material. In FIG. 31, like reference numerals are used to designate like parts appearing in FIG. 1.

Referring to FIG. 31, a measuring object 1 is a member such as a part of an equipment or a primary piping system of a plant such as a nuclear power plant. The apparatus includes an exciting coil 23 for magnetizing the measuring object 1, a superconducting quantum interference device 350 for detecting the magnetization, a magnetization control unit 4, a data processor 50, and a cooling device 410 for maintaining the superconducting quantum interference device 350 at its operating temperature.

The exciting coil 23 and the superconducting quantum interference device 350 are disposed opposite to the surface cf the measuring object 1. The exciting coil 23 is electrically connected to the magnetization control unit 4 which controls the process of magnetization. The superconducting quantum interference device 350 and the magnetization control unit 4 are electrically connected to the data processor 50, so that the data processor 50 receives data of magnetization and detected magnetization. A master curve used for decision of degradation of the metal material is previously prepared to deal with the above data, so that the degree of degradation of the measuring object 1 can be decided on the basis of the master curve.

Figure 32:
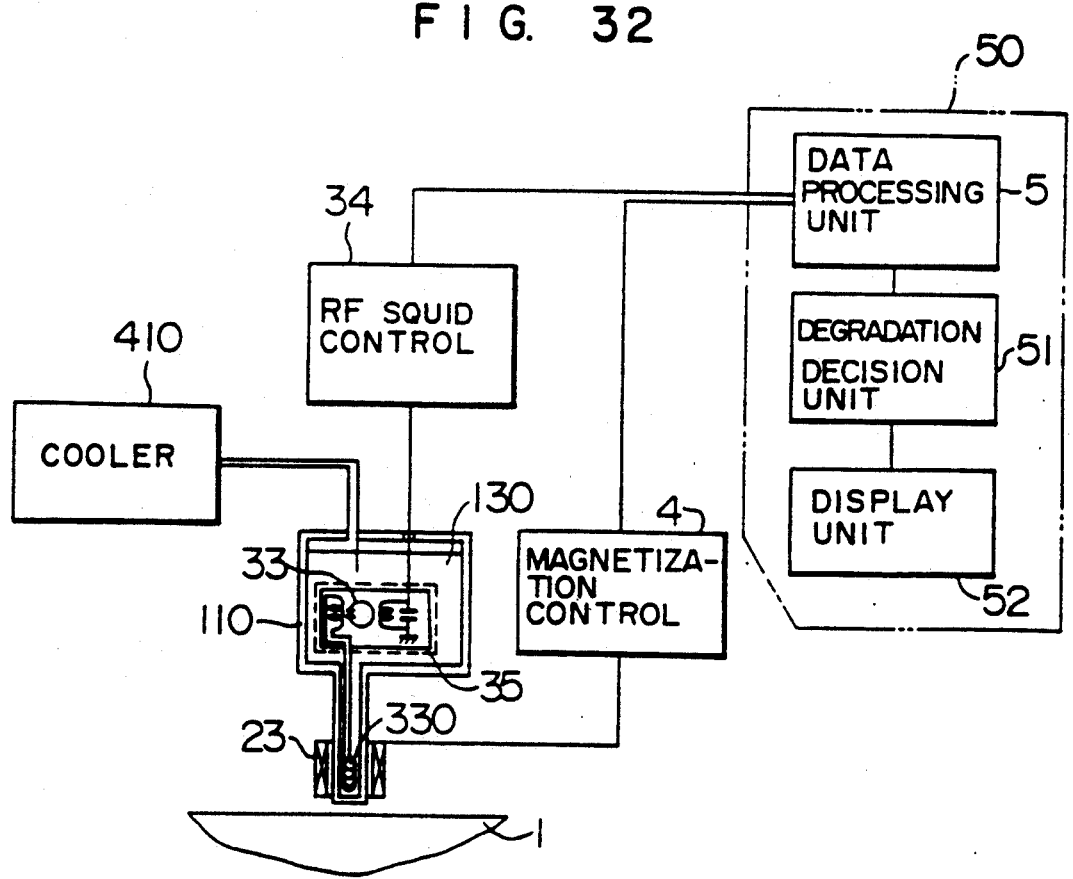
FIG. 32 shows in detail the system structure of the principal parts of the embodiment shown in FIG. 31.

FIG. 32 shows in detail the structure of the superconducting quantum interference device 350 and data processor 50. Referring to FIG. 32, an rf SQUID 33 is associated with a pickup coil 330 of a normal conducting material such as gold or silver and is controlled by an rf SQUID controller 34. The rf SQUID 33 is shielded by a combination magnetic shield and radiation shield 35. A container 110 of a non-magnetic heat insulating material is filled with a coolant 130 so as to maintain the rf SQUID 33 at its operating temperature.

The front end of the container 110 is shaped into the form of a small-diameter cylinder which is pressed onto the surface of the measuring object 1. The exciting coil 23 is wound around the outside surface of the cylindrical portion of the container 110, and the pickup coil 330 of the normal conducting material is placed inside the container 110. The measuring object 1 is magnetized by the exciting coil 23, and the rf SQUID 33 detects the changing magnetization through the pickup coil 330. The data indicative of the changing magnetization detected by the rf SQUID 33 is supplied to the data processor 50 under control of the rf SQUID controller 34.

The radiation shield 35 of a material such as lead is covered with a magnetic shield of a superconducting material so as to shield the rf SQUID 33 from external magnetic noise and radiations.

The measuring operation of the rf SQUID 33 provided with the pickup coil 330 of the normal conducting material will be described with reference to FIG. 33.

The measuring object 1 is magnetized to a level near the region of magnetic saturation by supplying a triangular waveform current to the exciting coil 23. As a result, the magnetic flux density B changes, and the magnetic hysteresis loop of the measuring object 1 shows a distorted waveform as shown in FIG. 33. The degree of degradation of the measuring object 1 is decided on the basis of such a distorted component of the waveform. However, the rf SQUID 33 cannot measure a magnetization as large as the magnetic saturation of the measuring object 1 although its resolution is high. Therefore, the pickup coil 330 is made of the normal conducting material, and an output signal as shown in FIG. 33 is obtained. That is, a signal indicative of the differentiated value of the detected change of the magnetization of the measuring object 1 is merely applied to the rf SQUID 33, and a signal indicative of a large magnetization is not applied to the rf SQUID 33.

The detailed structure of the data processor 50 will now be described. As shown in FIG. 32, the data processor 50 includes a data processing unit 5, a degradation decision unit 51 and a display unit 52.

The magnetic signal of the measuring object 1 measured by the rf SQUID 33 is processed by the data processing unit 5, and higher harmonic components and Barkhausen noise components of the magnetic signal are detected. The detected higher harmonic components and Barkhausen noise components are compared in the degradation decision unit 51 with master curves shown in FIGS. 34 and 35 respectively, and the results of comparison are converted into the degree of degradation in the degradation decision unit 51. The result of decision is displayed on the display unit 52.

According to the embodiment shown in FIG. 31, a change in the magnetization characteristic of a metal material can be detected with high accuracy. Therefore, a distortion of the magnetic field can be measured with high accuracy, and the accuracy of evaluation of the degree of degradation of the metal material can be improved.

SYSTEM ARRANGEMENT OF FIFTH EMBODIMENT

Figure 36:
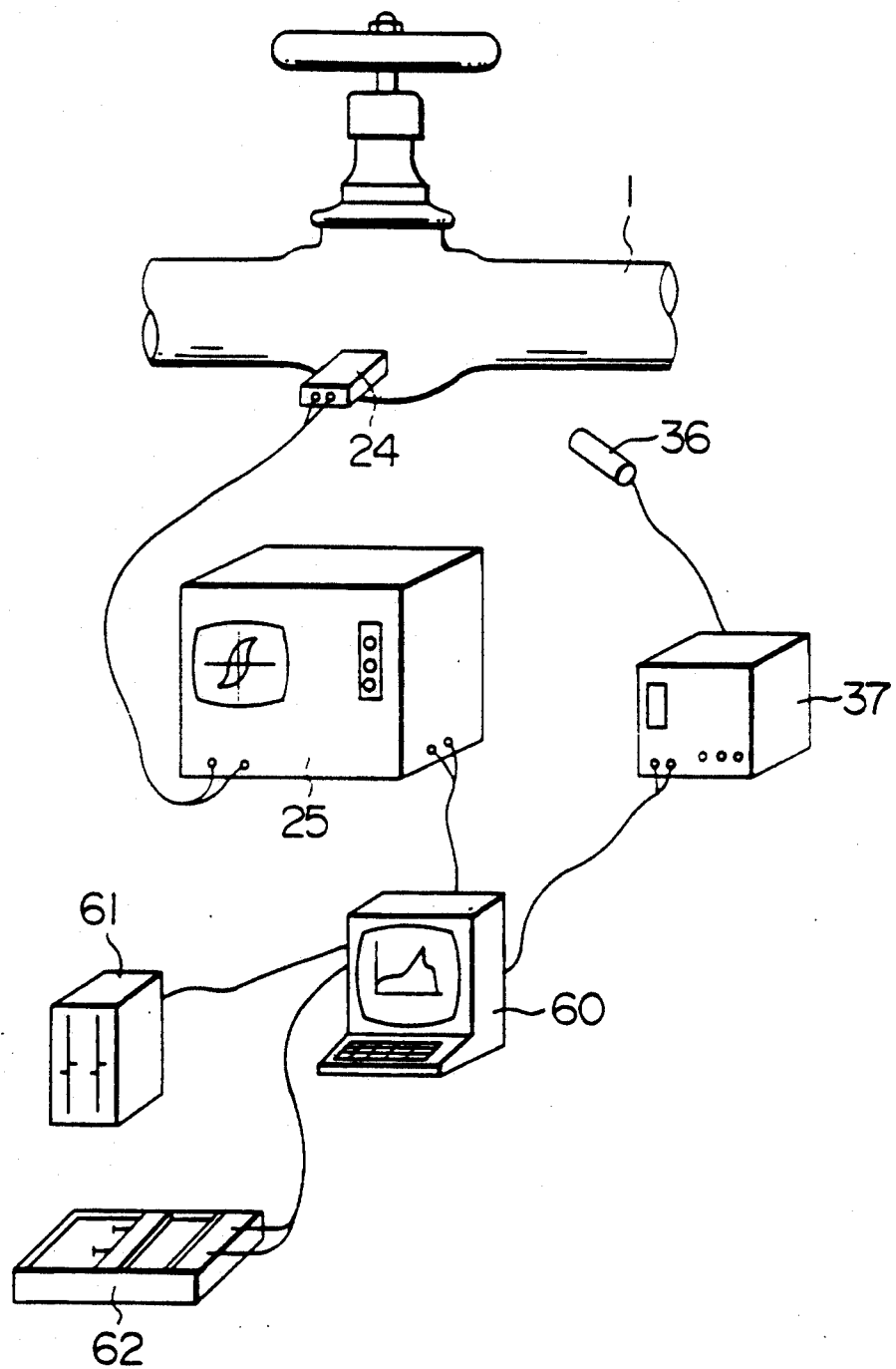
FIG. 36 is a schematic perspective view of a fifth embodiment of the present invention.

FIG. 36 shows a basic system arrangement employed for putting into practical use a fifth embodiment of the apparatus of the present invention for inspecting degradation of a metal material.

Referring to FIG. 36, a measuring object 1 whose secular degradation is to be measured is, for example, a valve casing of a metal material such as a duplex stainless steel. A magnetic field exciting coil 24 applies a predetermined saturation magnetic field to the measuring object 1 thereby producing a residual magnetism. The coil 24 is electrically connected to a device 25 which supplies a necessary voltage for producing the saturation magnetic field. A computer 60 controls the predetermined magnetic field and acts also to process data of the applied magnetic field. An external memory 61 and an external recorder 62 are connected to the computer 60.

After the saturation magnetic field is applied to the measuring object 1, the applied magnetic field is rendered null. Then, a high-sensitivity magnetization sensor 36 for sensing the residual magnetism is brought to a position close to the measuring object 1, and the sensed residual magnetism is measured by a magnetization detector 37. The signal indicative of the value of the detected residual magnetism is applied to the external memory 61 and external recorder 62.

The external memory 61 stores a data base of data representing the relation between various values of previously computed residual magnetism and the degree of degradation of the metal material. On the basis of the above relation, the computer 60 computes the value of rupture tenacity indicative of the degree of degradation of the measuring object 1.

Figure 40:
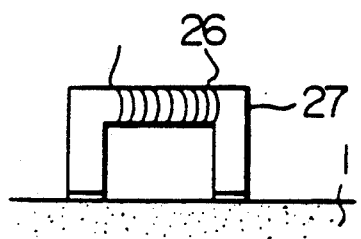
FIG. 40 schematically illustrates the basic structure of the magnetic field applying coil shown in FIG. 36.

FIG. 40 shows schematically the basic structure of the coil 24 applying the saturation magnetic field to the measuring object 1. As shown in FIG. 40, a coil 26 wound around an iron core 27 is moved toward the measuring object 1 to apply the magnetic field to the measuring object 1. The iron core 27 is preferably made of a ferromagnetic material, and a strong magnetic field can be produced when a superconducting material is used to form the coil 26. Cooling is required when such a superconducting coil is used. Therefore, a high-temperature superconducting coil is preferably used.

The magnetization sensor 36 is used for measuring the residual magnetism of the measuring object 1. Thus, when a high-sensitivity superconducting quantum interference device is used as part of the magnetization sensor 36, the residual magnetism can be measured with high accuracy, and even a minute change in the degree of degradation can be detected. When a high-temperature superconducting quantum interference device is used as the superconducting quantum interference device, the size of the cooler can be made small, and the magnetization sensor 36 can be made compact.

A semiconductor Hall element may be used as part of the magnetization sensor 36. Since the Hall element can directly detect a magnetic change in a metal material, the residual magnetism can be detected with high accuracy.

Figure 38:
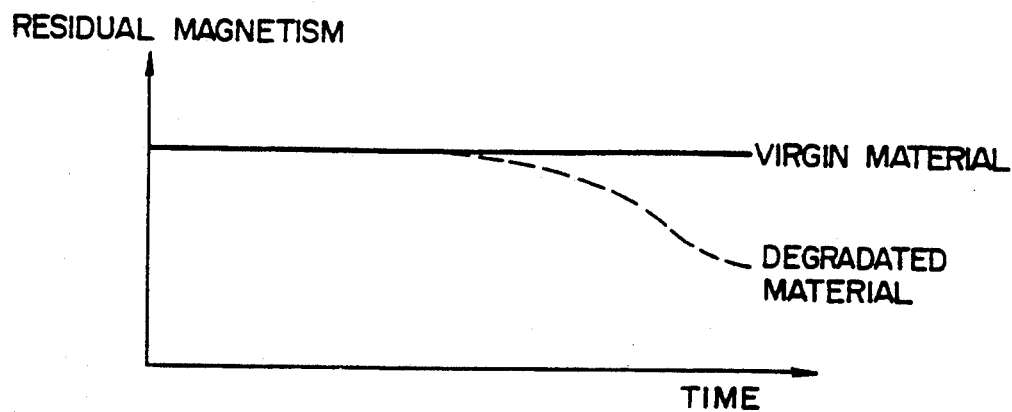
FIG. 38 is a graph showing how the residual magnetism of the degradated material changes with time relative to that of the unused virgin material.

When the residual magnetism of the measuring object 1 does not change for a long period of time after demagnetization as shown in FIG. 38, the measuring object 1 need not be magnetized to the level of the magnetic saturation again at the time of later detection of the residual magnetism.

The principle of operation of the fifth embodiment shown in FIG. 36 will be described with reference to FIG. 37.

When a metal material is used for a long period of time in an environment of a high temperature, a change occurs in its internal structure, resulting in a decreased mechanical strength. It is known that, as the internal structure changes, the electromagnetic characteristics such as the electrical resistivity $\rho$ and permeability $\mu$ of the metal material are subjected to a change, and the mechanical properties such as the hardness and metallographic structure of the metal material are also subjected to a change.

As a result of researches and studies on the tendency toward embrittlement of a metal material such as a duplex stainless steel due to heating at high temperatures, the inventors found that there was a correlation between the degree of embrittlement and the brittle-going characteristics of the stainless steel. By utilization of such a phenomenon, the degree of embrittlement of, for example, a weld of a duplex stainless steel or a ferritic stainless steel can be evaluated.

Figure 37:
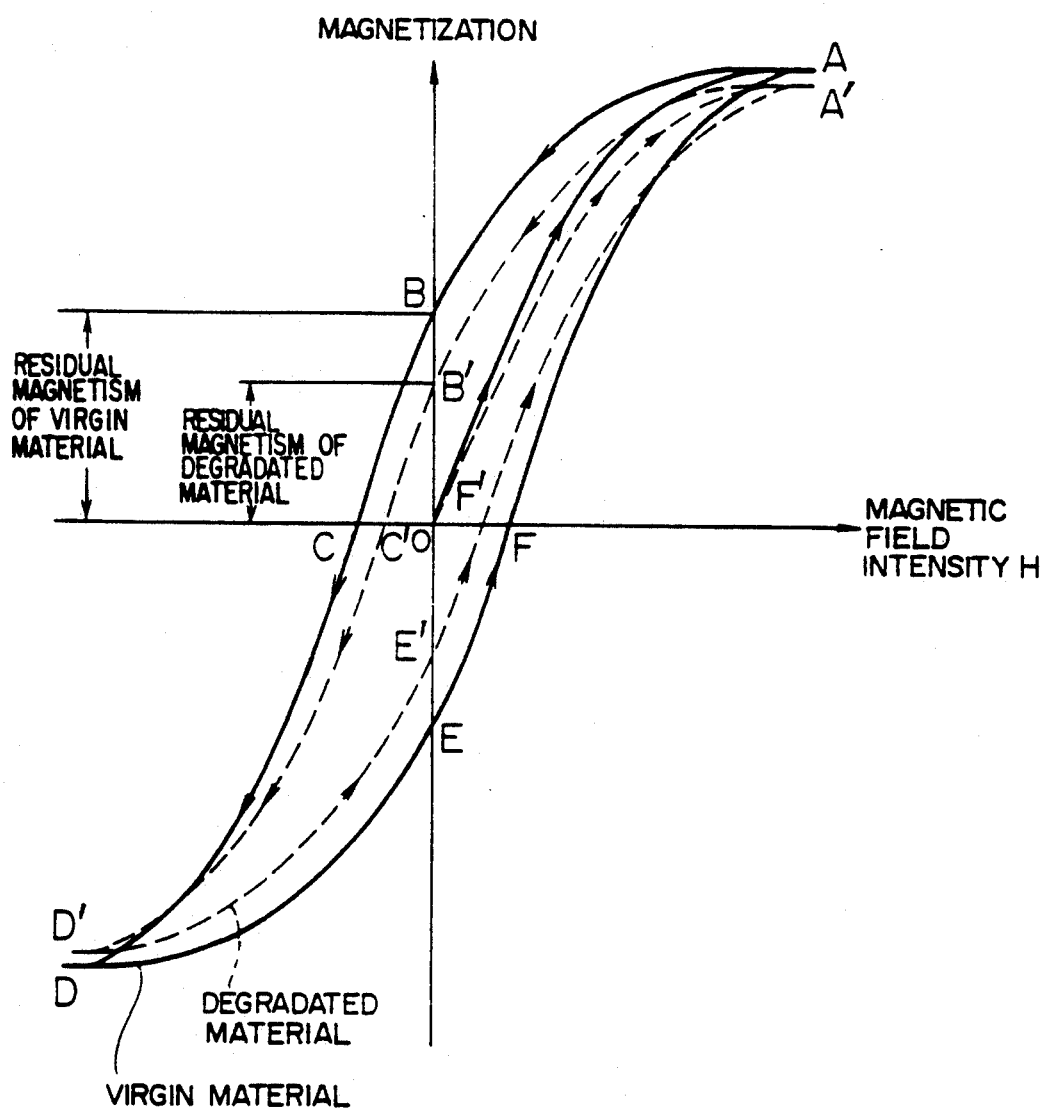
FIG. 37 shows a magnetic hysteresis of an unused virgin metal material compared to that of the metal material in a degradated state.

Describing more precisely, a magnetic metal material shows generally a magnetic hysteresis loop as shown in FIG. 37. When the strength of a magnetic field intensity H is increased from the value of zero magnetization, the magnetization M saturates at a point A. Then, when the strength of the magnetic field intensity H is decreased to zero from the point A, a residual magnetism OB remains. On the other hand, when the strength of the magnetic field H is increased, the residual magnetism becomes zero at the coercive force OC. Then, when the strength of the magnetic field H is further increased, magnetic saturation in the negative direction is reached at a point D.

In the magnetic hysteresis schematically shown in FIG. 37, the solid curve represents that of a virgin metal material before being subjected to secular degradation, while the dotted curve represents that of a metal having been subjected to secular degradation. As described already, the permeability $\mu$, residual magnetism OB and coercive force OC of a metal material such as a duplex stainless steel are subjected to a change when it is used for a long period of time at a high temperature.

Figure 39:
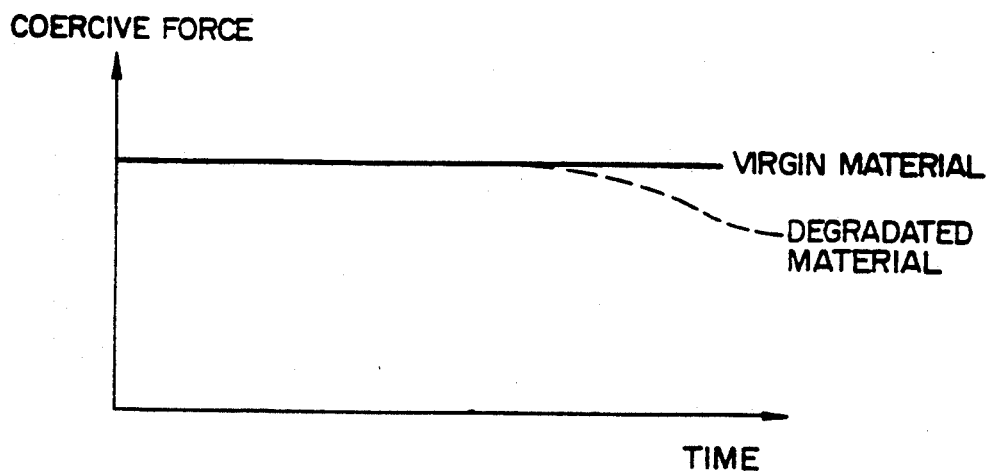
FIG. 39 is a graph showing how the coercive force of the degradated material changes with time relative to that of the unused virgin material.

FIG. 38 schematically shows how the residual magnetism of a virgin metal material and a degradated metal material change with time. It will be seen in FIG. 38 that, even when a magnetic field is applied to the virgin metal material, and the metal material is left to stand at the room temperature in that state, the residual magnetism does not appreciably change unless an affecting magnetic field is applied. On the other hand, when the virgin metal material is left to stand for a long period of time at a high temperature, the precipitate in the steel is subjected to a change, resulting in a corresponding change in the residual magnetism. This tendency applies also to the coercive force. FIG. 39 shows similar changes in the coercive force relative to time.

The residual magnetism of the virgin material and that of the degradated material are measured by the magnetization sensor 36, and the degree of degradation of the metal material due to exposure to a high temperature for a long period of time is decided on the basis of the relation between the previously computed change in the residual magnetism of the metal material and the fracture toughness of the metal material. The coercive force may be measured in lieu of the residual magnetism.

We claim:

1. A degradation detecting apparatus comprising means for applying a magnetic field to a measuring object including an exciting coil in the form of a superconducting system and an exciting power source connected thereto, and a magnetization characteristic measuring device for measuring a magnetization characteristic of said measuring object so as to detect the degree of degradation of said measuring object on the basis of a change in said magnetization characteristic of said measuring object due to application of said magnetic field, said magnetization characteristic measuring device including a magnetization sensor disposed at the center of said exciting coil, said sensor being operable at low temperatures, a fluidtight container of a heat insulating material containing the entirety of at least said exciting coil and said magnetization sensor, and a cooling system for cooling the superconducting system, said detecting apparatus further comprising means for previously computing relation between the magnetization characteristic and degradation of a reference object and for comparing the detected magnetization characteristic of said measuring object with said relation to decide the degree of degradation of said measuring object at the time of detection, wherein said means for previously computing the relation between the magnetization characteristic and degradation of said reference object and for comparing the detected magnetization characteristic of said measuring objects with said relation to decide the degree of degradation of said measuring object at the time of detection includes storage means for storing a data base of previously acquired data of the relation between changes in the magnetization characteristic an degradation of said reference object, a first arithmetic processing part for estimating magnetization characteristic of said measuring object in an as-received material on the basis of the data stored in said data base, and a second arithmetic processing part computing the change from said estimated magnetization characteristic to said detected magnetization characteristic on the basis of the data stored in said data base to generate the degree of degradation of said measuring object as an output.

* * * * *